(12) United States Patent
Kapoor et al.

(10) Patent No.: US 11,920,196 B2
(45) Date of Patent: Mar. 5, 2024

(54) CIRCULATING MICRORNAS IN KNEE OSTEOARTHRITIS AND USES THEREOF

(71) Applicant: University Health Network, Toronto (CA)

(72) Inventors: Mohit Kapoor, Pickering (CA); Rajiv Gandhi, Toronto (CA); Shabana Amanda Ali, Windsor (CA)

(73) Assignee: University Health Network, Toronto (CA)

( * ) Notice: Subject to any disclaimer, the term of this patent is extended or adjusted under 35 U.S.C. 154(b) by 79 days.

(21) Appl. No.: 17/337,163

(22) Filed: Jun. 2, 2021

(65) Prior Publication Data

US 2021/0381047 A1 Dec. 9, 2021

Related U.S. Application Data

(60) Provisional application No. 63/033,463, filed on Jun. 2, 2020.

(51) Int. Cl.
*C12Q 1/6876* (2018.01)

(52) U.S. Cl.
CPC ..... *C12Q 1/6876* (2013.01); *C12Q 2600/178* (2013.01)

(58) Field of Classification Search
None
See application file for complete search history.

(56) References Cited

U.S. PATENT DOCUMENTS

| 2016/0024575 A1* | 1/2016 | Spindler | C12Q 1/6886 435/243 |
| 2017/0009295 A1* | 1/2017 | Rigoutsos | C12Q 1/6886 |

OTHER PUBLICATIONS

Lai (Medicine 2019 98:51).*
Murata (Arthritis Research and Therapy 2010 12:R86).*
Mompeon (Scientific Reports Mar. 25, 2020 10:5373).*
Ghorai (Frontiers in Genetics Apr. 2014 vol. 5 article 100).*
Murata, Koichi et al. Plasma and synovial fluid microRNAs as potential biomarkers of rheumatoid arthritis and osteoarthritis, Murata et al. Arthritis Reserach & Therapy 2010, 12:R86.
Cuadra, Veronica M. Borgonio et al. Altered Expression of Circulating MicroRNA in Plasma of Patients with Primary Osteoarthritis and In Silico Analysis of Their Pathways, PLOS one, Jun. 2014, vol. 9, Issue 6, e97690.
Beyer, Christian et al. Signature of circulating microRNAs in osteoarthritis, Ann Rheum Dis 2015; 74:e 18.
Ntoumou, E et al. Serum microRNA array analysis identifies miR-140-3p, miR-33b-3p and miR-671-3p as potential osteoarthritis biomarkers involved in metabolic processes, Ntoumou et al. Clinical Epigenetics (2017) 9:127.
Aae, Tommy Froseth et al. Evaluating plasma extracellular vesicle microRNAs as possible biomarkers for osteoarthritis, Osteoarthritis and Cartilage Open 1 (2020) 100018.
Rousseau, Jean-Charles et al. Association of circulating microRNAs with prevalent and incident knee osteoarthritis in women: the OFELY study, Rousseau et al. Arthritis Research & Therapy, (2020) 22:2.
Ali, S.A. et al. Osteoarthritis and Cartilage. Osteoarthritis Research Society International. 28 (2020) 1471-1481.

* cited by examiner

*Primary Examiner* — Amanda Haney
(74) *Attorney, Agent, or Firm* — Bereskin & Parr LLP; Carmela De Luca

(57) ABSTRACT

A method comprising obtaining a substantially cell-free sample of blood plasma or blood serum from a subject with osteoarthritis; and detecting a presence of or measuring a level of novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and novel_miRNA_4 (uaguggguuaucagaacu) (SEQ ID NO: 4). Also provided are methods where additional miRNAs are detected including novel miRNA 5 (SEQ ID NO: 5), novel miRNA 6 (SEQ ID NO: 6), novel miRNA 7 (SEQ ID NO: 7), novel miRNA 8 (SEQ ID NO: 8), novel miRNA 9 (SEQ ID NO: 9), novel miRNA 10 (SEQ ID NO: 10), novel miRNA 11 (SEQ ID NO: 11), novel miRNA 12 (SEQ ID NO: 12), novel miRNA 13 (SEQ ID NO: 13), hsa-miR-335-3p, hsa-miR-199a-5p, hsa-miR-671-3p, hsa-miR-1260b, hsa-miR-191-3p, hsa-miR-335-5p and/or hsa-miR-543.

22 Claims, 9 Drawing Sheets
Specification includes a Sequence Listing.

Fig. 4

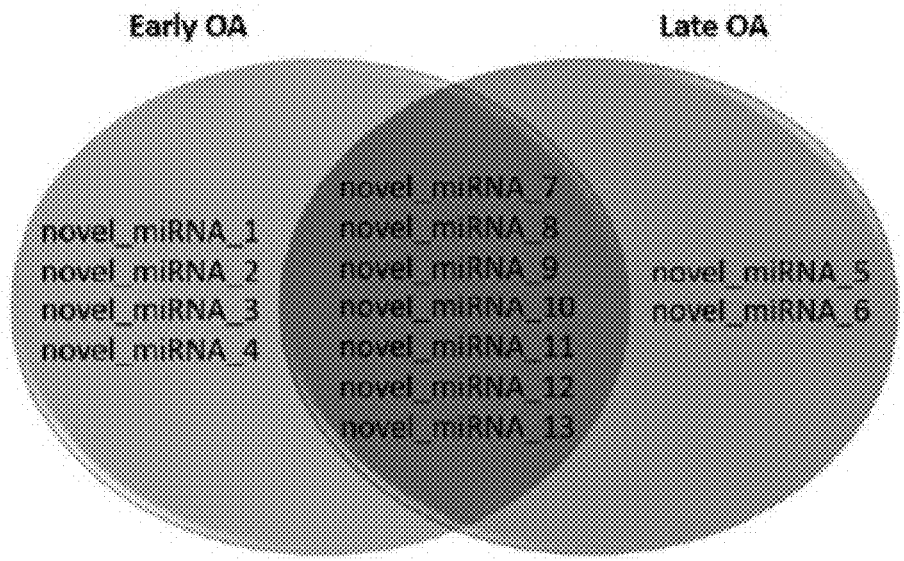

| Novel miRNA | Sequence | Early OA (n=41) | Late OA (n=50) | Londin et al., 2015 | |
|---|---|---|---|---|---|
| novel_miRNA_1 | gucuggcucagggauggg | 56 (N=23) | 36 (N=18) | Absent | SEQ ID NO: 1 |
| novel_miRNA_2 | uccuguucgggrgccacu | 68 (N=28) | 20 (N=10) | Absent | SEQ ID NO: 2 |
| novel_miRNA_3 | uguuuagcauccuguagccugc | 59 (N=24) | 4 (N=2) | Present | SEQ ID NO: 3 |
| novel_miRNA_4 | uagugggúuaucagaacu | 66 (N=27) | 14 (N=7) | Absent | SEQ ID NO: 4 |
| novel_miRNA_5 | acugagggaugaaggaucagg | 31 (N=13) | 50 (N=25) | Present | SEQ ID NO: 5 |
| novel_miRNA_6 | caugaauggauuaaugag | 44 (N=18) | 50 (N=25) | Absent | SEQ ID NO: 6 |
| novel_miRNA_7 | ugguccaacgacaggagúagg | 58 (N=24) | 86 (N=43) | Present | SEQ ID NO: 7 |
| novel_miRNA_8 | gaugccugggaguugcgaucug | 51 (N=21) | 92 (N=46) | Absent | SEQ ID NO: 8 |
| novel_miRNA_9 | uuaguggcucccucugccugca | 80 (N=33) | 86 (N=43) | Present | SEQ ID NO: 9 |
| novel_miRNA_10 | aggaagguggggaugacg | 66 (N=27) | 80 (N=40) | Absent | SEQ ID NO: 10 |
| novel_miRNA_11 | uugaggucggacaugguggcu | 93 (N=38) | 92 (N=46) | Absent | SEQ ID NO: 11 |
| novel_miRNA_12 | acuagggauggggaau | 58 (N=24) | 60 (N=30) | Absent | SEQ ID NO: 12 |
| novel_miRNA_13 | aggagugggaggagaaug | 66 (N=27) | 66 (N=33) | Absent | SEQ ID NO: 13 |

| microRNA (n=3) | logFC | logCPM | FDR | Proportion |
| --- | --- | --- | --- | --- |
| hsa-miR-193b-5p | -1.34 | 3.59 | 0.002 | 0.62 |
| hsa-miR-193a-5p | -1.01 | 6.52 | 0.004 | 0.52 |
| hsa-miR-455-5p | -2.74 | 1.44 | 0.000 | 0.50 |

CIRCULATING MICRORNAS IN KNEE OSTEOARTHRITIS AND USES THEREOF

RELATED APPLICATION

This application claims priority to U.S. Provisional Patent Application 63/033,463 filed Jun. 2, 2020, which is herein incorporated by reference in its entirety.

SEQUENCE LISTING

A computer readable form of the Sequence Listing "10723-P61196US01 Sequence Listing_ST25.txt" (2,177 bytes), submitted via EFS-WEB and created on Jun. 2, 2021, is herein incorporated by reference.

FIELD

The disclosure relates to methods and compositions of reagents for detecting circulating miRNAs differentially present in different stages of knee osteoarthritis.

BACKGROUND

The complex pathophysiology of osteoarthritis (OA) results from an interplay between systemic and local joint factors (1). There are relatively few large-scale studies with clearly defined patient cohorts profiling molecular differences in circulating factors in OA, particularly in early stages of disease. Identification of novel molecular targets in early stages of disease may uncover strategies for intervention while opportunities still exist to prevent progression to end stages. To better understand the pathophysiology of early stages of OA, there is an urgent need to create well-characterized early OA cohorts and to conduct comprehensive molecular profiling of circulating factors.

Next generation sequencing has emerged as the gold standard approach for profiling molecular targets in biospecimens of interest in both health and disease. Sequencing offers the sensitivity and specificity to detect novel transcripts and low abundance isoforms that may be unique to particular disease stages (2). Decreases in the cost of sequencing have made this approach more feasible for analyzing large datasets, providing the statistical power needed to consider multiple patient factors alongside molecular factors. As the technology advances, applications are expanding, and now include sequencing of small non-coding RNAs such as microRNAs.

MicroRNAs are small non-coding ribonucleic acid (RNA) molecules that inhibit expression of their gene targets (3). Potentially important biomarkers for disease, peripheral blood microRNAs are abundant, relatively stable, and detectable through minimally invasive means (4, 5). MicroRNAs play key roles in OA pathophysiology (6), having been identified in several human joint tissues and fluids including knee and hip cartilage (7), synovium (8), spine cartilage (9), synovial fluid (10) and plasma (11). While previous studies have identified circulating microRNAs in OA (11-16), to the best of our knowledge, sequencing has never been applied to identify circulating microRNA signatures between early and late symptomatic radiographic knee OA.

SUMMARY

Provided are methods including a method staging of knee osteoarthritis (OA) comprising a) obtaining a substantially cell-free sample of blood plasma or blood serum from a subject with knee osteoarthritis;
b) detecting a presence of or measuring a level of one or more miRNAs selected from hsa-miR-335-3p, hsa-miR-199a-5p, hsa-miR-671-3p, hsa-miR-1260b, hsa-miR-191-3p, hsa-miR-335-5p, hsa-miR-543, novel_miRNA_1 (gucuggcucagggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and novel_miRNA_4 (uagugg-guuaucagaacu) (SEQ ID NO: 4); and
c) identifying the subject as likely to have early stage osteoarthritis or late stage osteoarthritis based on the presence of or measured level of the one or more miRNAs.

Isolated nucleic acids, primers, probes, panels and kits are also provided.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 4 shows novel microRNAs identified in early OA and late OA plasma. Sequences for 13 novel microRNAs that were expressed in 50% or more of samples within each group (Early OA or Late OA). Frequencies (%) and n values are provided for each group and each microRNA, with only those in 50% or more of samples shown in black. Sequences for novel microRNAs were cross-referenced to those reported by Londin et al. (21) and indicated as 'Present' if previously reported or 'Absent' if not.

DETAILED DESCRIPTION OF THE DISCLOSURE

Figure 1:
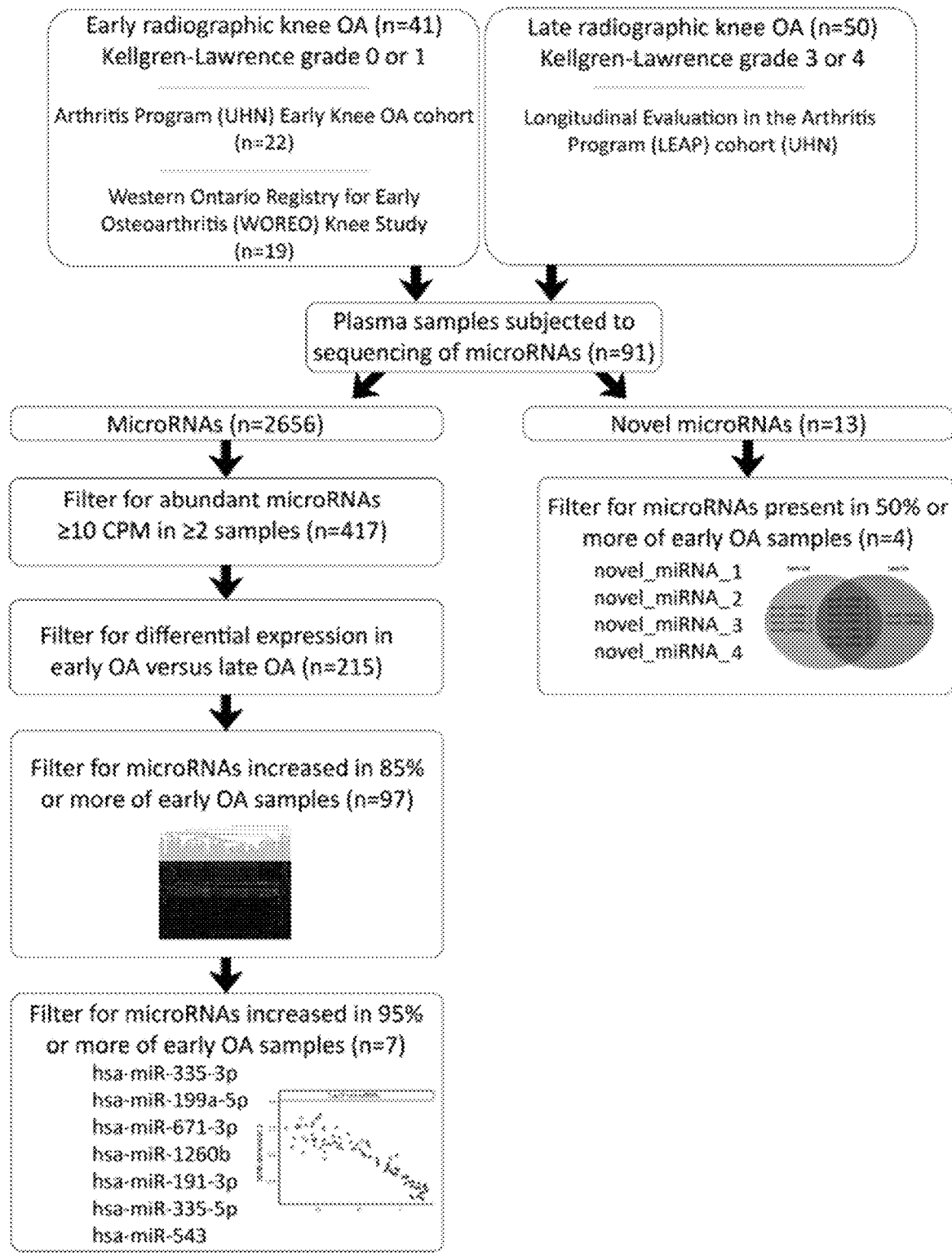
FIG. 1 is a schematic overview of experimental workflow. Cohorts of early OA (n=41) and late OA (n=50) were subjected to sequencing of microRNAs isolated from blood plasma. Sequential filtration of microRNAs resulted in the final lists used for computational analyses to predict gene targets and pathways.

As described herein, sequencing was used to profile circulating microRNAs in blood plasma from 91 patients with symptomatic knee OA (17) as diagnosed by a rheumatologist or orthopaedic surgeon and as staged using Kellgren-Lawrence (KL) radiographic grading (18). The early radiographic knee OA cohort (n=41; referred to as 'early OA') included patients with KL grades 0 or 1, and the late radiographic knee OA cohort (n=50; referred to as 'late OA') included patients with KL grades 3 or 4. Patients with KL grade 2 were excluded in order to clearly differentiate the early OA group from the late OA group. In this large sequencing dataset (19), rigorous statistical approaches were used to consider multiple covariates, including age, sex, race, and body mass index (BMI), which are known to impact both OA pathophysiology and microRNA profiles (20). Applying sequencing technology, a distinct signature of plasma microRNAs in early OA was identified, consisting of 7 microRNAs and 4 previously unknown microRNAs. With an integrated computational biology approach, putative downstream gene targets and pathways modulated by this microRNA signature in early OA were identified.

Accordingly described herein is a microRNA signature in human blood plasma that is associated with early radiographic stages of knee osteoarthritis (OA), that includes for example one or more of microRNAs: hsa-miR-335-3p, hsa-miR-199a-5p, hsa-miR-671-3p, hsa-miR-1260b, hsa-miR-191-3p, hsa-miR-335-5p, hsa-miR-543, novel_miRNA_1 (gucuggcucagggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and/or novel_miRNA_4 (uaguggguuaucagaacu) (SEQ ID NO: 4).

The current approach for diagnosis of OA relies on radiographs. This is limited since the appearance of radiographic features often means opportunities for intervention have been missed to diagnose knee OA in early stages. This is useful since there is currently no blood test to detect OA.

Isolated nucleic acids, panels, kits, compositions and methods related thereto are described.

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The term "early osteoarthritis" as used herein means symptomatic knee osteoarthritis staged by Kellgren & Lawrence radiographic grade 0 or 1.

The term "late osteoarthritis" as used herein means knee osteoarthritis with detectable structural changes as staged by Kellgren & Lawrence radiographic grade 3 or 4

The term "sequence identity" as used herein refers to the percentage of sequence identity (also referred to herein as "percent identity") between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions·times·100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, word-length=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. The percent identity between two sequences can be determined using techniques similar to those described above, with or without allowing gaps. In calculating percent identity, typically only exact matches are counted.

The term "nucleic acid" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil as well as inosine. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The nucleic acids can for example or comprise one or more locked nucleic acid (LNA) moieties. The term "isolated nucleic acid molecules" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

The term "detectable label" as used herein refers to moieties such as peptide sequences, fluorescent proteins that can be appended or introduced into a peptide, antibody or other compound described herein and which is capable of producing, either directly or indirectly, a detectable signal. For example, the label may be radio-opaque, or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin. For example, the detectable label may be one useful for qPCR or microarray.

The term "hsa" as used herein refers to Homo sapiens.

It is understood that although a sequence or SEQ ID NO is provided in a particular format e.g. DNA or RNA, the other is understood to be encompassed according to the context as would be understood by a person skilled in the art. For example, is understood that RNA typically includes uracil, whereas DNA typically included thymidine in place thereof.

Nucleic Acids, Compositions, Panels and Kits

An aspect provides a nucleic acid molecule, optionally an isolated nucleic acid molecule, comprising a target sequence of any one of novel_miRNA_1 to novel_miRNA_13, for example novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), novel_miRNA_4 (uagugguuaucagaacu) (SEQ ID NO: 4), a cDNA thereof, a complementary sequence of any of the foregoing, or a sequence with at least 80% sequence identity to any of the foregoing. In some embodiments, the nucleic acid molecule is a DNA, optionally a cDNA, or a RNA. A target sequence can be part, optionally 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides of a miRNA sequence, or the full length of a miRNA sequence.

In some embodiments the nucleic acid molecule is single stranded. In other embodiments the nucleic acid is double stranded. When double stranded the nucleic acid may have a blunt end or an overhang (e.g. a single stranded portion). In some embodiments, the double stranded nucleic acid has at least one blunt end, optionally two blunt ends. In some embodiments, the double stranded nucleic acid lacks a 3' overhang of 2 nucleotides, e.g has one or no nucleotide overhang at its 3' end. In other embodiments, the double stranded nucleic acid comprises a 1 or 2 nucleotide overhang, optionally a 3' overhang. In some embodiments, the dsRNA is a DNA-RNA complex, optionally a complex comprising a miRNA strand, optionally one or more of the miRNA as described herein, and a complementary DNA strand. FIG. 4 identifies miRNAs and whether they were previously identified (e.g. in Londin 2015 (21). In some embodiments, the nucleic acid molecule, optionally in a DNA-RNA complex, comprises at least one and up to 4 mismatches to a miRNA. In some embodiments, the DNA-RNA complex comprises 1 mismatch, 2 mismatches, 3 mismatches or 4 mismatches. In some embodiments, the nucleic acid molecule has at least one and up to 4 mutations, optionally 1 mutation, 2 mutations, 3 mutations, or 4 mutations.

In an embodiment, the sequence with at least 80% sequence identity hybridizes to the target sequence (e.g. any one of novel_miRNA_1 to novel_miRNA_13, for example novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), novel_miRNA_4 (uagugguuaucagaacu) (SEQ ID NO: 4)) or its complement.

In some embodiments the nucleic acid molecule, optionally isolated nucleic acid molecule comprises the sequence of any one of novel_miRNA_1 (SEQ ID NO: 1) to novel_miRNA_5 (SEQ ID NO: 5) or novel_miRNA_7 (SEQ ID NO: 7) to novel_miRNA_13 (SEQ ID NO: 13).

In some embodiments the nucleic acid molecule, optionally isolated nucleic acid molecule comprises the sequence selected from the group comprising novel_miRNA_1 (SEQ ID NO: 1), novel_miRNA_2 (SEQ ID NO: 2), novel_miRNA_4 (SEQ ID NO: 4), novel_miRNA_6 (SEQ ID NO: 6), novel_miRNA_8 (SEQ ID NO: 8), and novel_miRNA_10 (SEQ ID NO: 10) to novel_miRNA_13 (SEQ ID NO: 13).

In some embodiments the nucleic acid molecule, optionally isolated nucleic acid molecule, comprises the sequence selected from the group comprising novel_miRNA_1 (SEQ ID NO: 1), novel_miRNA_2 (SEQ ID NO: 2), novel_miRNA_4 (SEQ ID NO: 4), novel_miRNA_8 (SEQ ID NO: 8), and novel_miRNA_10 (SEQ ID NO: 10) to novel_miRNA_13 (SEQ ID NO: 13).

In some embodiments the nucleic acid molecule, optionally isolated nucleic acid molecule, comprises the sequence selected from the group comprising novel_miRNA_1 (SEQ ID NO: 1), novel_miRNA_2 (SEQ ID NO: 2), novel_miRNA_3 (SEQ ID NO: 3), and novel_miRNA_4 (SEQ ID NO: 4).

In some embodiments the nucleic acid molecule, optionally isolated nucleic acid molecule, comprises the sequence selected from the group comprising novel_miRNA_1 (SEQ ID NO: 1), novel_miRNA_2 (SEQ ID NO: 2), and novel_miRNA_4 (SEQ ID NO: 4).

In some embodiments the nucleic acid molecule, optionally isolated nucleic acid molecule, comprises the sequence of novel_miRNA_1 (SEQ ID NO: 1).

In some embodiments the nucleic acid molecule, optionally isolated nucleic acid molecule, comprises the sequence of novel_miRNA_2 (SEQ ID NO: 2).

In some embodiments the nucleic acid molecule, optionally isolated nucleic acid molecule, comprises the sequence of novel_miRNA_4 (SEQ ID NO: 4).

In an embodiment, the nucleic acid molecule, optionally isolated nucleic acid, is a probe, optionally a RNA probe, a DNA probe optionally double stranded and optionally labelled, for example radiolabeled or nonisotopically labelled. Such probes can be prepared for example using mirVana™ miRNA Probe Construction kits. In one embodiment, the probe comprise a DNA polynucleotide comprising a nucleic acid specific for a miRNA described herein and an primer complementary portion, for example, an 8 base sequence complementary to the 3' end of the T7 promoter primer.

In an embodiment, nucleic acid molecule, optionally the isolated nucleic acid, is a primer. The primer can comprise a tag or nucleic acid portion comprising a restriction endonuclease site, for use in cloning. Primer pairs can also be used, for example, for a miRNA that is 22 bps, a 12-18 nucleotide long forward primer and a reverse primer with 3-8 specific nucleotides at the 3' end and an extension that is for example complementary to a universal tag, added to the template during cDNA synthesis can be used. In some embodiments, the primer, optionally a forward primer or a reverse primer, can be anywhere from 12 to 25 nucleotides or longer. In some embodiments, the primer, optionally a forward primer or a reverse primer, is complementary to at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides or more of a miRNA described herein.

The primer can be LNA enhanced primer or probe or combination thereof. For example, miRCURY™ LNA miRNA probe primer sets can be used, such as those available from Qiagen.

The primers and probes can be used to detect a target sequence, for example in a method described herein. In some embodiments, the primers or probes comprise at least one and up to 4 mismatches to a miRNA. In some embodiments, the primers or probes comprise 1 mismatch, 2 mismatches, 3 mismatches or 4 mismatches to a miRNA.

In some embodiments, the nucleic acid, optionally a primer or probe or sets thereof, is in a composition, optionally lyophilized.

The nucleic acid molecule, for example the probe, can be labelled with a detectable label.

Also provided is a composition comprising any of the isolated nucleic acids described herein and optionally a carrier or diluent. In some embodiments, the composition is lyophilized.

The diluent can for example be water, saline or other nucleic acid suitable diluent.

For example, the composition can comprise an isolated nucleic acid sequence comprising any one of novel_miRNA_1 to novel_miRNA_13, for example novel_miRNA_1 (gucuggcucagggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), novel_miRNA_4 (uaguggguuaucagaacu) (SEQ ID NO: 4), a cDNA thereof, a complementary sequence of any of the foregoing, or a sequence with at least 80% sequence identity to any of the foregoing.

The composition can comprise one or more nucleic acids comprising a sequence selected from hsa-miR-335-3p, hsa-miR-199a-5p, hsa-miR-671-3p, hsa-miR-1260b, hsa-miR-191-3p, hsa-miR-335-5p and hsa-miR-543, a cDNA thereof, a complementary sequence of any of the foregoing, or a sequence with at least 80% sequence identity to any of the foregoing. In an embodiment, the sequence with at least 80% sequence identity hybridizes to the target sequence. The compositions can comprise one or more probes or primers for detecting and/or measuring a level of one or more miRNAs selected from hsa-miR-335-3p, hsa-miR-199a-5p, hsa-miR-671-3p, hsa-miR-1260b, hsa-miR-191-3p, hsa-miR-335-5p and hsa-miR-543.

In one embodiment, the composition comprises one or more of the nucleic acids (miRNAs) described herein (e.g. Table 2B and/or 2C) a cDNA thereof, a complementary sequence of any of the foregoing, or a sequence with at least 80% sequence identity to any of the foregoing. In another embodiment, the composition comprises one or more probes or primers for detecting and/or measuring a level of one or more miRNAs described herein. The sequences for the miRNAs are available in mirbase available at www.mirbase.org release v. 22.1.

In some embodiments the composition comprises one or more of one or more of the isolated nucleic acids molecules, primers or probes described herein and a diluent or carrier.

The composition can also comprise other primers or probes that are useful in detection. For example the composition can comprise a miRNA specific primer and a detection probe, e.g. a non miRNA specific probe, optionally a TaqMan™ probe.

In some embodiments the composition comprises at least two of the isolated nucleic acids molecules, primers or probes described herein.

In some embodiments the composition comprises at least two of the isolated nucleic acids molecules described herein.

In some embodiments the composition comprises the isolated nucleic acid molecules are one or more of novel_miRNA_1 to novel_miRNA_13.

In some embodiments the composition comprises the isolated nucleic acid molecules are one or more of novel_miRNA_1 to novel_miRNA_5 or novel_miRNA_7 to novel_miRNA_13.

In some embodiments the composition comprises the isolated nucleic acid molecules are one or more of novel_ miRNA_1, novel_miRNA_2, novel_miRNA_4, novel_miRNA_6, novel_miRNA_8, and novel_miRNA_10 to novel_ miRNA_13.

In some embodiments the composition comprises the isolated nucleic acid molecules are one or more of novel_miRNA_1, novel_miRNA_2, novel_miRNA_4, novel_miRNA_8, and novel_miRNA_10 to novel_miRNA_13.

In some embodiments the composition comprises the isolated nucleic acid molecules are one or more of novel_miRNA_1, novel_miRNA_2, novel_miRNA_3, and novel_miRNA_4.

In some embodiments the composition comprises the isolated nucleic acid molecules are one or more of novel_miRNA_1, novel_miRNA_2, and novel_miRNA_4.

In some embodiments the composition comprises the isolated nucleic acid molecules are one or more of novel_miRNA_1.

In some embodiments the composition comprises the isolated nucleic acid molecule is novel_miRNA_2.

In some embodiments the composition comprises the isolated nucleic acid molecule is novel_miRNA_4.

Also provided is a panel comprising a solid surface, optionally a chip, plate, bead, slide, or miRNA card, comprising two or more detection agents, each for detecting a miRNA described herein. For example the panel can comprise probes or primers for detecting or measuring the level of one or more of novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), novel_miRNA_4 (uaguggguuaucagaacu) (SEQ ID NO: 4), hsa-miR-335-3p, hsa-miR-199a-5p, hsa-miR-671-3p, hsa-miR-1260b, hsa-miR-191-3p, hsa-miR-335-5p and hsa-miR-543. The panel can comprise one or more additional detection agents for detecting or measuring the levels of any one of the miRNAs in Table 2B and/or 2C. In some embodiments the panel is a microarray. In some embodiments, the plate is a 96 well plate.

Provided in another aspect is a kit for detecting one or more of the miRNAs described herein, for example one or more of novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), novel_miRNA_4 (uaguggguuaucagaacu) (SEQ ID NO: 4), hsa-miR-335-3p, hsa-miR-199a-5p, hsa-miR-671-3p, hsa-miR-1260b, hsa-miR-191-3p, hsa-miR-335-5p and hsa-miR-543, and optionally one or more of the of the miRNAs in Table 2B and/or 2C. The kit can comprise one or more nucleic acid molecules, primers, probes or compositions or panels described herein, and optionally one or more reagents for collecting a blood sample or isolating a fraction from blood such as a plasma or serum fraction, and/or one or more reagents or devices for isolating and quantifying miRNA. The kit can also be for use in a method described herein.

Blood samples can be collected in K2-EDTA tubes and centrifuged at 4000 rpm for 10 minutes at 4° C. The resulting plasma supernatant can be aliquotted for example into 250 uL per cryovial, flash frozen with liquid nitrogen, and stored in a cryo freezer until use.

In one embodiment, the nucleic acid molecule is RNA. In another embodiment, the nucleic acid molecule is DNA. In a further embodiment, the nucleic acid molecule comprises one or more modified bases or is a DNA/RNA a hybrid.

One or more of the above components can be used in a method described herein.

Methods

As described herein, a number of unknown miRNAs were identified and isolated. Accordingly, an aspect provides a method comprising:

(a) obtaining a substantially cell-free sample of blood plasma or blood serum from a subject with knee osteoarthritis;

(b) detecting the presence of or measuring the level of one or more of novel_miRNA_1, novel_miRNA_2, novel_miRNA_3, novel_miRNA_4, novel_miRNA_5, novel_miRNA_6, novel_miRNA_7, novel_miRNA_8, novel_miRNA_9, novel_miRNA_10, novel_miRNA_11, novel_miRNA_12, or novel_miRNA_13.

As indicated herein, various miRNAs were associated with early stage or late stage knee osteoarthritis. No blood test for detecting early knee osteoarthritis is available.

Accordingly, another aspect provides a method staging of osteoarthritis (OA) comprising:

(a) obtaining a substantially cell-free sample of blood plasma or blood serum from a subject with knee osteoarthritis;

(b) detecting a presence of or measuring a level of one or more miRNAs selected from hsa-miR-335-3p, hsa-miR-199a-5p, hsa-miR-671-3p, hsa-miR-1260b, hsa-miR-191-3p, hsa-miR-335-5p, hsa-miR-543, novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and novel_miRNA_4 (uaguggguuaucagaacu) (SEQ ID NO: 4); and (c) identifying the subject as likely to have early stage osteoarthritis or late stage osteoarthritis based on the presence of or measured level of the one or more miRNAs.

In one embodiment, the method comprises detecting the presence of or measuring the level of one or more of novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and novel_miRNA_4 (uaguggguuaucagaacu) (SEQ ID NO: 4).

A substantially cell-free sample of blood plasma or blood serum can be obtained by processing a blood sample that was obtained from a patient as described in the Examples. Substantially as used herein means that at least 90%, 95%, 98%, 99% or more of the cells have been removed.

In one embodiment, the method comprises detecting the presence of or measuring the level of one or more of hsa-miR-335-3p, hsa-miR-199a-5p, hsa-miR-671-3p, hsa-miR-1260b, hsa-miR-191-3p, hsa-miR-335-5p and/or hsa-miR-543.

In one embodiment, the method comprises detecting the presence of or measuring the level of at least 2, at least 3, at least 4, at least 5, at least 6, at least 7, at least 8, at least 9, at least 10, or at least 11 miRNAs. Any number of the miRNAs in Table 2B and/or 2C can be detected and/or measured.

In one embodiment, the method comprises detecting the presence of or measuring the level of hsa-miR-335-3p, hsa-miR-199a-5p, hsa-miR-671-3p, hsa-miR-1260b, hsa-miR-191-3p, hsa-miR-335-5p, hsa-miR-543, novel_miRNA_1 (gucuggcucaggguuggg) (SEQ ID NO: 1), novel_miRNA_2 (ucccuguucgggcgccacu) (SEQ ID NO: 2), novel_miRNA_3 (uguuuagcauccuguagccugc) (SEQ ID NO: 3), and novel_miRNA_4 (uaguggguuaucagaacu) (SEQ ID NO: 4).

miRNAs can be detected and measured using a variety of methods known in the art. In some embodiments, known miRNA can be detected and measured using for example the ThermoFisher TaqMan™ MicroRNA Assay (for example for detecting and measuring hsa-miR-335*). In some embodiments, miRNAs can be detected and measured using real-time PCR and next generation sequencing, optionally using library preparation and sequencing analysis to determine the expression microRNAs of interest as described herein. In some embodiments, miRNAs can be detected using RNA sequencing (RNA-Seq), microarrays or PCR such as reverse transcription PCR, for example RT-qPCR. In some embodiments, the miRNA is detected using a microarray, wherein a target nucleic acid, (for example, a miRNA described herein) hybridizes with a probe, optionally a DNA probe, optionally resulting in a DNA-RNA complex. The target nucleic acid can be labelled, optionally a fluorescent label, during poly A tail extension and levels of fluorescent are detected and indicate the presence and/or levels of the target nucleic acid. Further details on the use of microarrays for detecting miRNAs can be found for example in Krepelkova et al, 2019 (49), which is incorporated by reference.

In some embodiments, miRNAs can be detected using PCR optionally reverse transcription PCR, for example RT-qPCR. In some embodiments, miRNAs, optionally one or more of the miRNAs described herein can be reverse transcribed, creating a cDNA, the presence of which is then identified or the level of which is then quantified using PCR, optionally qPCR. Further details on the use of reverse transcription PCRs for detecting miRNAs can be found for example in Krepelkova et al, 2019, which is incorporated by reference.

In some embodiments, miRNAs can be detected and measured using methods using ligase based methods such as SplintR®-qPCR. In some embodiments, miRNAs, optionally one or more of the miRNAs described herein can be can be detected and measured by synthesizing a cDNA by enzymatic ligation of two DNA oligonucleotides splinted by target miRNA, optionally using Chlorella virus DNA ligase (SplintR® ligase), the presence of which is then identified or the level of which is then quantified using PCR, optionally qPCR. In some embodiments SplintR®-qPCR can be used where a 4-6 base pair overlap between a DNA probe and miRNA is present. Further details on SplintR®-qPCR for detecting miRNAs can be found for example in Krepelkova et al. 2019, which is incorporated by reference.

In some embodiments, miRNAs can be detected and measured using an miRNA immunoassay such as miREIA. In some embodiments, miRNAs, optionally one or more of the miRNAs described herein can be can be detected and measured by using a unique monoclonal antibody specific to DNA/RNA complexes, for example the complex which results when a target RNA, optionally a miRNA, optionally a miRNA described herein, hybridizes to a DNA probe, followed by the subsequent identification and/or quantification of generated the DNA/RNA, optionally DNA/miRNA complexes. Further details on immunoassays for detecting miRNAs can be found for example in Krepelkova et al., 2019, which is incorporated by reference.

The step of identifying the subject as likely to have early stage osteoarthritis or late stage osteoarthritis based on the presence of or measured level of the one or more miRNAs can comprise comparing the measured level of the one or more miRNAs to a reference level. For example the reference can be a median level in a known stage population for example as determined in the Examples. In some embodiments, the subject is identified as likely to have early stage osteoarthritis if the level of one or more of hsa-miR-335-3p, hsa-miR-199a-5p, hsa-miR-671-3p, hsa-miR-1260b, hsa-miR-191-3p, hsa-miR-335-5p and/or hsa-miR-543 is increased compared to a reference level, optionally the median level in a late stage osteoarthritis reference population.

In an embodiment, the method comprises detecting or measuring the level of hsa-miR-335-3p. In an embodiment, the subject is identified as likely to have early stage osteoarthritis if the level of hsa-miR-335-3p is increased compared to a reference level, optionally the median level in a late stage osteoarthritis reference population.

In an embodiment, the increase compared to the reference level indicative of a stage is at least two fold (e.g. test level is at least 2× the reference value), 5 fold, 10 fold, 20 fold or 30 fold or greater.

In some embodiments, the method further comprising detecting the presence of or measuring the level of one or more of other miRNAs in Table 2B and/or Table 2C.

Table 2B identifies 97 miRNAs that were increased or decreased in early stage osteoarthritis compared to late stage osteoarthritis.

Table 2C identifies 3 miRNAs that were increased in late stage osteoarthritis compared to early stage osteoarthritis.

The detecting or measuring can comprise use of one or more probes, such as nucleic acid probes, optionally cDNA probes or stabilized RNA probes that hybridize to the target miRNA. The probe can be for example at least 80% or at least 90% sequence identity to the complement of a miRNA.

The detecting or measuring can comprise use or RT-PCR, optionally quantitative RT-PCR, microarray and/or sequencing.

Methods for sequencing miRNAs is provided in Examples 2 and 3. One or more of these steps can be used.

In some embodiments, the method is for detecting early stage osteoarthritis.

Also provided in another aspect is a method of producing a miRNA library. The method comprises one or more of the steps described in the Example 2 or 3.

In one embodiment, a method described herein comprises one or more steps described herein related to blood sample acquisition, microRNA isolation, sequencing, read alignment, unique molecular index (UMI) analysis, counts generation, normalization, and statistical and bioinformatics approaches applied as described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

Example 1

Summary

Sequencing large patient cohorts offers the sensitivity and specificity to detect novel and low abundance microRNAs that may be unique to disease stages. We apply sequencing to identify signatures of circulating microRNAs in patients with early and late symptomatic radiographic knee osteoarthritis. Early osteoarthritis was defined as Kellgren-Lawrence grade 0 or 1 (n=41), and late osteoarthritis as Kellgren-Lawrence grade 3 or 4 (n=50). After sequencing microRNAs isolated from plasma samples, counts were produced for microRNAs captured in miRBase and for novel microRNAs. We found 97 microRNAs with an increase or decrease in expression in ≥85% of samples in the early osteoarthritis group as compared to the median expression in the late osteoarthritis group. Increasing this threshold to ≥95%, 7 microRNAs were identified, including hsa-miR-335-3p, hsa-miR-199a-5p, hsa-miR-671-3p, hsa-miR-1260b, hsa-miR-191-3p, hsa-miR-335-5p, and hsa-miR-543. Four microRNAs were present in ≥50% of early osteoarthritis samples and had 27 gene targets in common with the prioritized set of gene targets from the 97 microRNAs, including SMAD2 and associated TGF-beta signaling pathway.

Methods are provided in Example 2 and Example 3.

Results

Establishing a Pipeline for Sequencing microRNAs in Human OA Plasma

Figure 6:
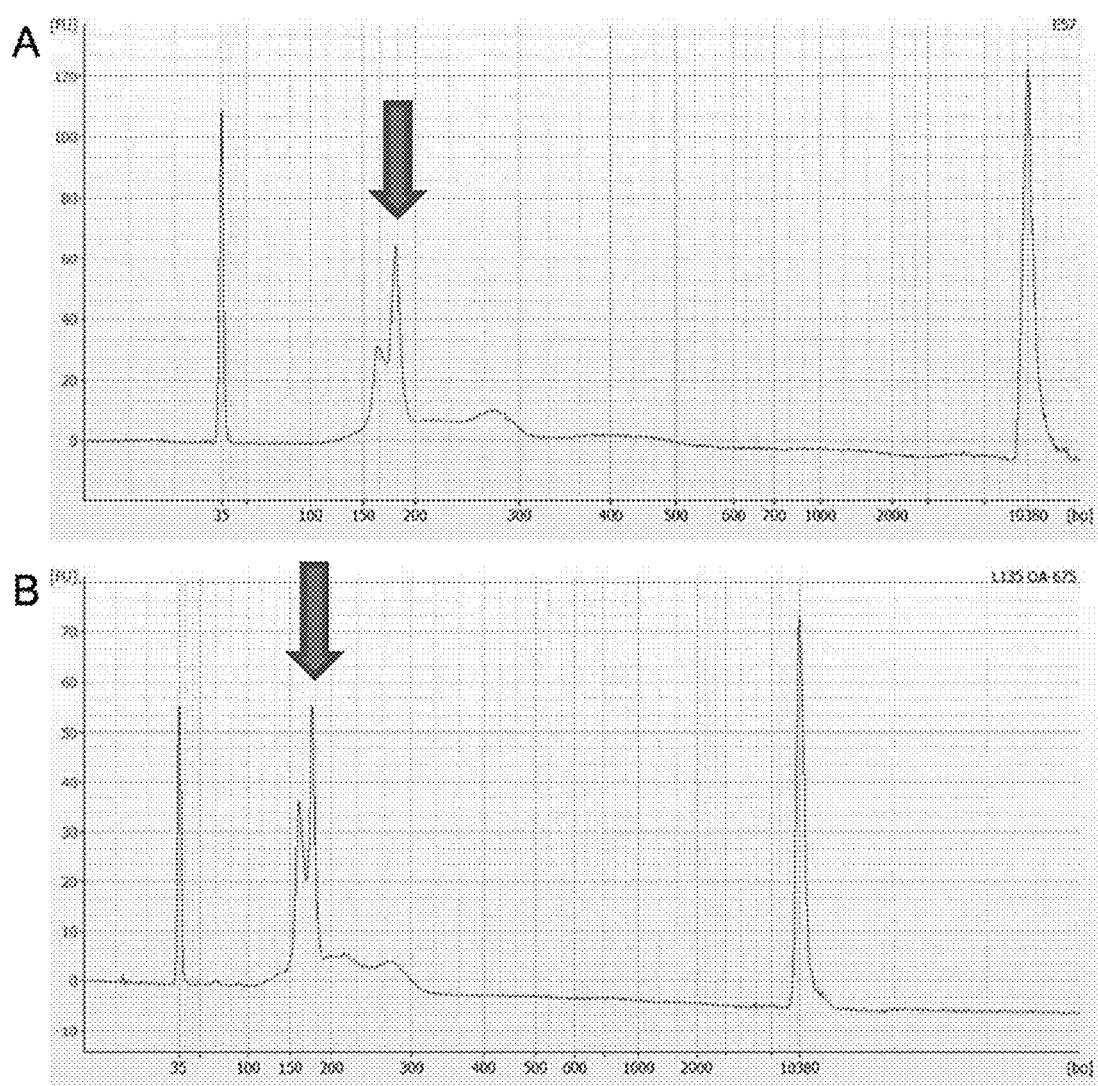
FIGS. 6A and B are representative BioAnalyzer traces from microRNA libraries prepared for sequencing. Y axis shows fluorescence units (FU) and x axis shows library size in bases (bp). Arrow points to microRNA library, predicted by QIAseq miRNA Library Kit to be 180 bp.

The microRNA-sequencing pipeline we used was optimized for high quality and carefully documented to support reproducibility (FIG. 1). A limitation of existing sequencing studies is the lack of granularity in reporting sequencing methods and data analysis used to produce final results. In addition to describing our cohorts (Table 1), we provide detailed methods for blood sample acquisition, microRNA isolation, library preparation, quality control assessment, sequencing, read alignment, unique molecular index (UMI) analysis, counts generation, normalization, and statistical and bioinformatics approaches applied. RNA containing microRNAs was isolated from blood plasma of 99 patients with OA and subjected to microRNA library preparation (see Example 3 for detailed protocol). Fluorometric quantification determined the mean concentration (±SD) of early OA libraries (n=49) was 18.6±4.4 ng/uL and late OA libraries (n=50) was 19.1±4.0 ng/uL. Library integrity assessment determined the average library size of early OA samples was 182±3 bp and late OA samples was 181±2 bp (FIG. 6).

Figure 5:
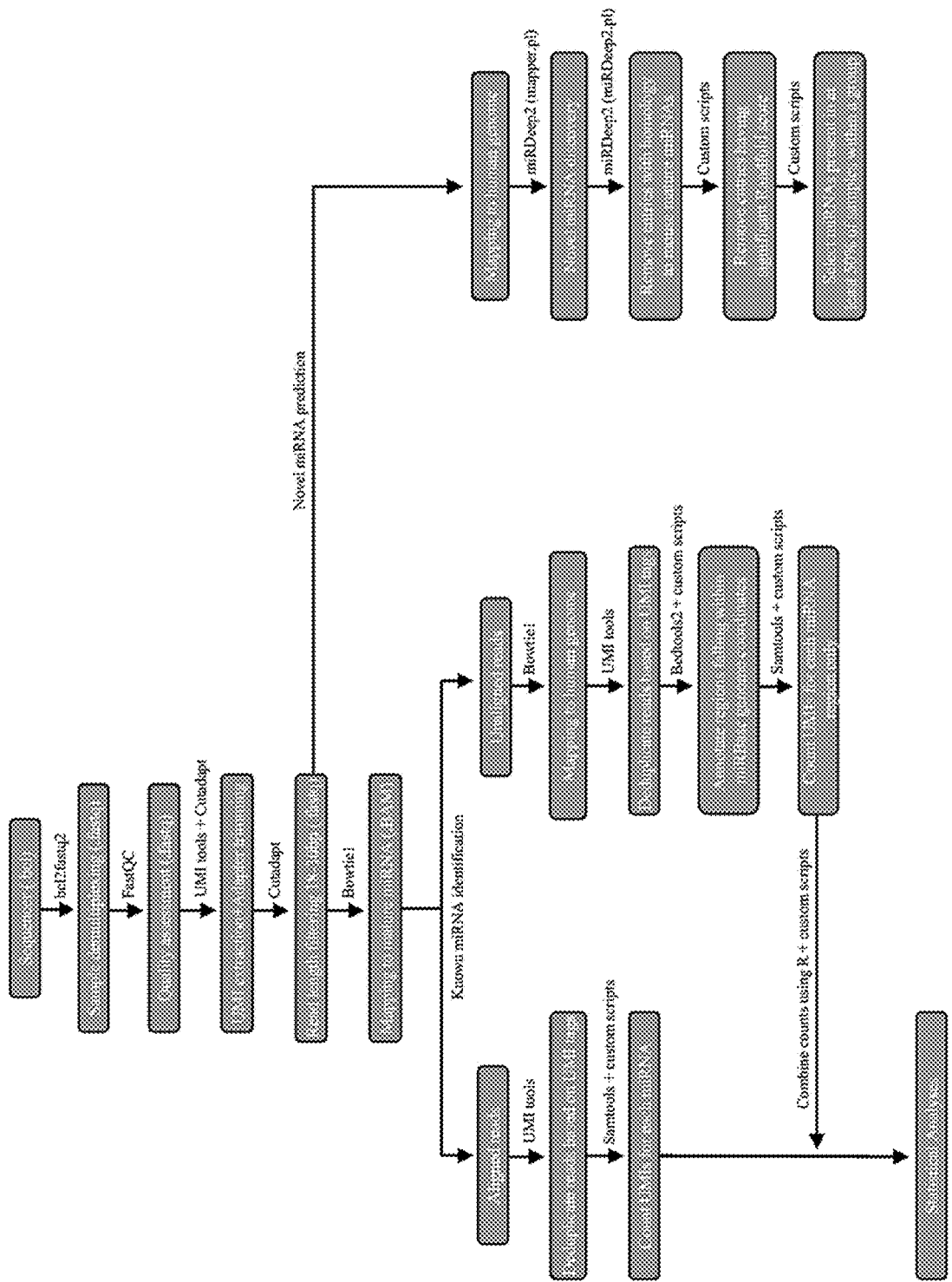
FIG. 5 is a pipeline schematic of methods used to generate counts from raw microRNA-sequencing data.
Figure 7:
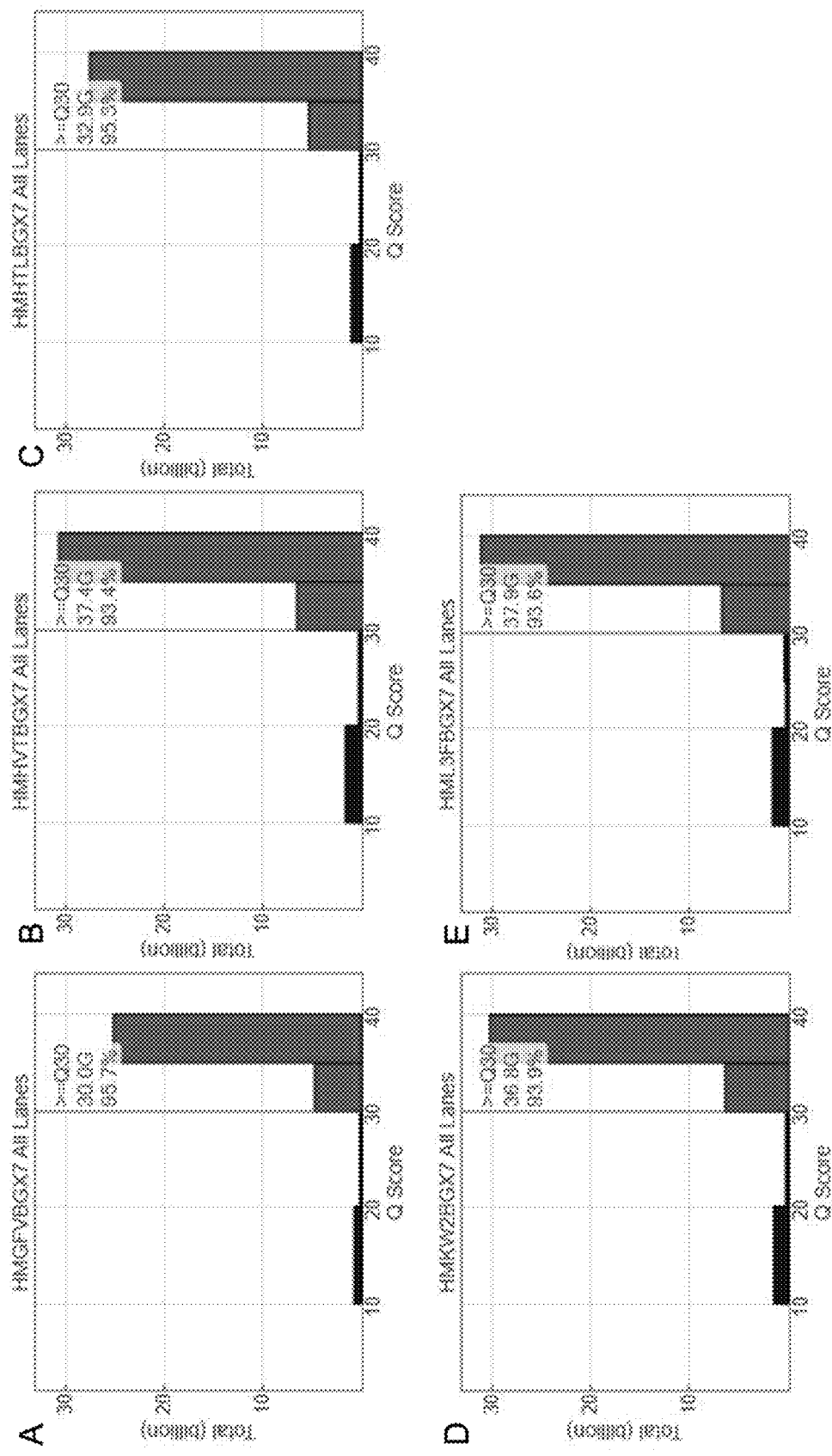
FIG. 7 A to E are Q-Score plots from sequencing runs. Sample libraries were divided into batches across 5 sequencing runs each containing early and late OA samples. Plots from each of 5 sequencing runs (A-E) show that the majority of reads have a Q-score above 30.

Libraries were sequenced and quality assessment of the runs revealed high quality (mean Q30 of 94.4%±1.2 SD) and high yield (35G±3 SD passing filter; FIG. 7). This resulted in >13±2 SD million raw reads per sample and an average of 2.0±1.2 SD million mapped reads per sample. Eight samples from the early OA group yielded fewer than 400,000 mapped reads and were excluded, resulting in n=41 early OA samples for subsequent analysis. UMI analysis was performed to account for library amplification bias (FIG. 5). The use of UMIs represents an improvement in the ability to estimate the absolute levels of profiled targets. Counts generated for all 2,656 microRNAs from miRBase v22.1 were normalized by total counts and filtered for microRNAs with at least 10 counts-per-million (CPM) reads in at least 2 samples, resulting in 417 microRNAs (table 2A).

Identifying a Panel of Circulating microRNAs in Early Radiographic Knee OA

Early and late OA cohorts were carefully characterized by sex, age, BMI, and race, where BMI was considered as both a continuous and categorical variable (Table 1).

TABLE 1

Patient characteristics. Frequencies (%) are provided for categorical variables while mean (standard deviation = SD) and median (min, max) are presented for continuous variables in the full cohort (n = 91) and for the early OA versus late OA groups. Non-parametric Kruskal-Wallis tests are applied for comparisons of continuous variables. Chi-square tests are applied for comparisons of categorical variables. Shown in bold are statistically significant p-values.

| Covariate | Total (n = 91) | KL0/1 (n = 41) | KL3/4 (n = 50) | p-value |
|---|---|---|---|---|
| SEX | | | | 0.55 |
| Female | 49 (54) | 24 (59) | 25 (50) | |
| Male | 42 (46) | 17 (41) | 25 (50) | |
| AGE | | | | 0.001 |
| Mean (sd) | 59.5 (13.6) | 50.4 (13.6) | 66.9 (8.1) | |
| Median (Min, Max) | 61 (24, 85) | 52 (24, 76) | 67 (51, 85) | |
| BMI CON | | | | 0.35 |
| Mean (sd) | 27.7 (4.5) | 27.3 (4.9) | 28 (4.2) | |
| Median (Min, Max) | 26.7 (19.9, 44.6) | 26 (19.9, 44.6) | 26.9 (21, 38.4) | |
| BMI CAT | | | | 0.51 |
| Normal | 29 (32) | 15 (37) | 14 (28) | |
| Obese | 25 (27) | 9 (22) | 16 (32) | |
| Overweight | 37 (41) | 17 (41) | 20 (40) | |
| RACE | | | | 0.022 |
| Non-Caucasian | 20 (22) | 14 (34) | 6 (12) | |
| Caucasian | 71 (78) | 27 (66) | 44 (88) | |
| WOMAC CON | | | | 0.053 |
| Mean (sd) | 48.7 (23.7) | 55.1 (27.9) | 43.9 (18.9) | |
| Median (Min, Max) | 48 (0, 100) | 50 (9, 100) | 40 (0, 82) | |
| Missing | 3 | 3 | 0 | |
| WOMAC CAT | | | | 0.029 |
| High | 45 (51) | 25 (66) | 20 (40) | |
| Low | 43 (49) | 13 (34) | 30 (60) | |
| Missing | 3 | 3 | 0 | |
| SEX | | | | 0.55 |
| Female | 49 (54) | 24 (59) | 25 (50) | |
| Male | 42 (46) | 17 (41) | 25 (50) | |
| AGE | | | | 0.001 |
| Mean (sd) | 59.5 (13.6) | 50.4 (13.6) | 66.9 (8.1) | |
| Median (Min, Max) | 61 (24, 85) | 52 (24, 76) | 67 (51, 85) | |

TABLE 1-continued

Patient characteristics. Frequencies (%) are provided for categorical variables while mean (standard deviation = SD) and median (min, max) are presented for continuous variables in the full cohort (n = 91) and for the early OA versus late OA groups. Non-parametric Kruskal-Wallis tests are applied for comparisons of continuous variables. Chi-square tests are applied for comparisons of categorical variables. Shown in bold are statistically significant p-values.

| Covariate | Total (n = 91) | KL0/1 (n = 41) | KL3/4 (n = 50) | p-value |
|---|---|---|---|---|
| BMI | | | | 0.35 |
| Mean (sd) | 27.7 (4.5) | 27.3 (4.9) | 28 (4.2) | |
| Median (Min, Max) | 26.7 (19.9, 44.6) | 26 (19.9, 44.6) | 26.9 (21, 38.4) | |
| BMI Category | | | | 0.51 |
| Normal | 29 (32) | 15 (37) | 14 (28) | |
| Overweight | 37 (41) | 17 (41) | 20 (40) | |
| Obese | 25 (27) | 9 (22) | 16 (32) | |
| RACE | | | | 0.022 |
| Non-White | 20 (22) | 14 (34) | 6 (12) | |
| White | 71 (78) | 27 (66) | 44 (88) | |

Figure 2:
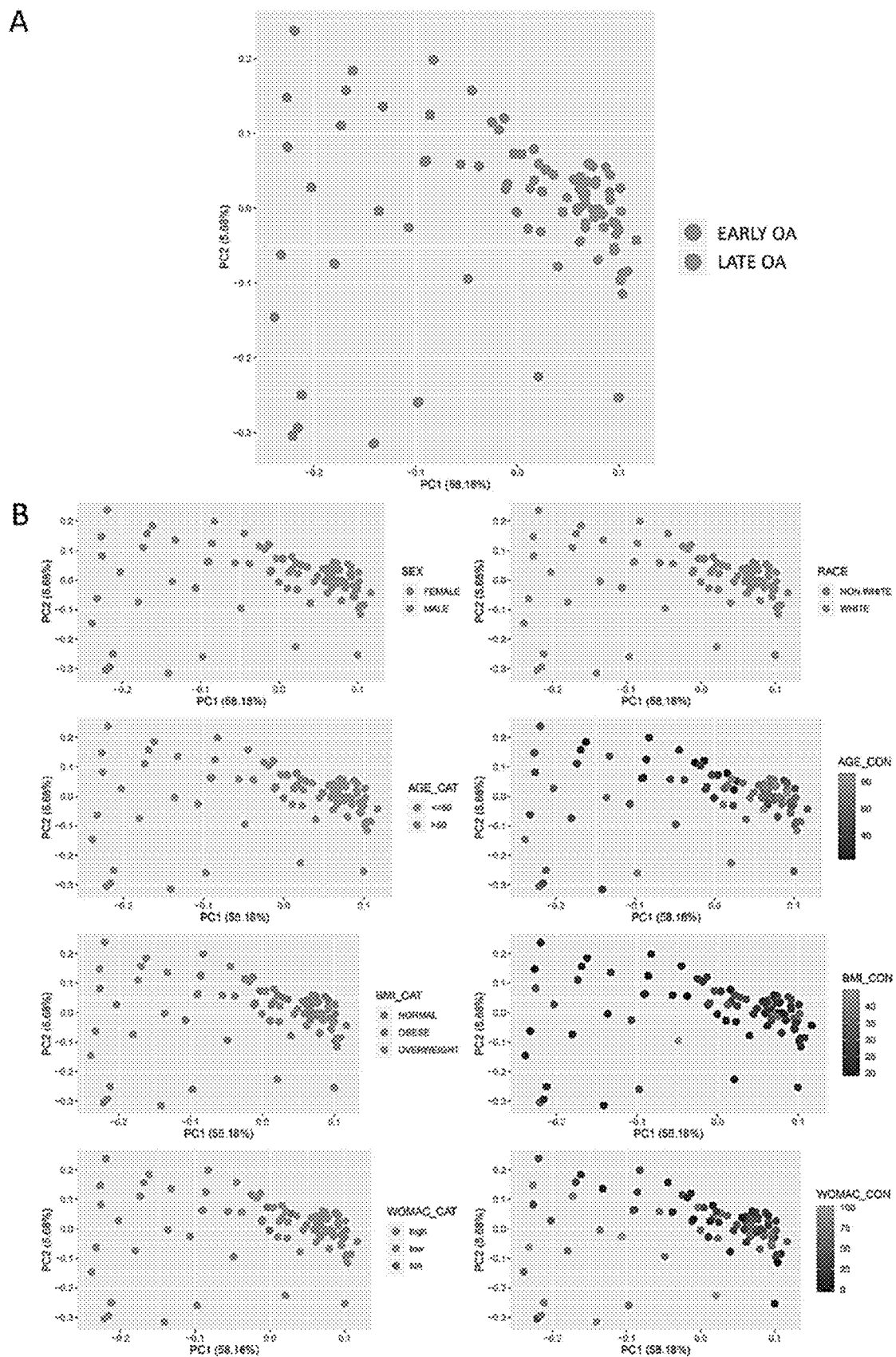
FIG. 2 is a clustering analysis of microRNA sequencing data. (A) Principal component analysis plot with points coloured according to early OA or late OA. (B) Principal component analysis plot with points coloured according to (L-R) sex, race, age categorical (AGE_CAT), age continuous (AGE_CON), BMI categorical (BMI_CAT; 18.5-24.9=normal; 25-29.9=overweight; 30+=obese), BMI continuous (BMI_CON).

As the first step, overall patterns in the sequencing data from early and late OA cohorts were visualized in an unbiased manner through dimensionality reduction and principal component analysis. From this, a distinct cluster of late OA samples emerged, clearly separating from the early OA samples (FIG. 2A). Separation to this degree was not observed for any of the other variables considered, including sex, race, age, and BMI, whether considered as a categorical or continuous variable (FIG. 2B). Age and race were identified as significantly different between groups (Table 1; p<0.05), and in the second step were included as factors in multivariate models used to determine differential expression of microRNAs in early OA versus late OA. Using a false discovery rate (FDR) threshold of less than 0.01, 215 microRNAs were identified.

Figure 3:
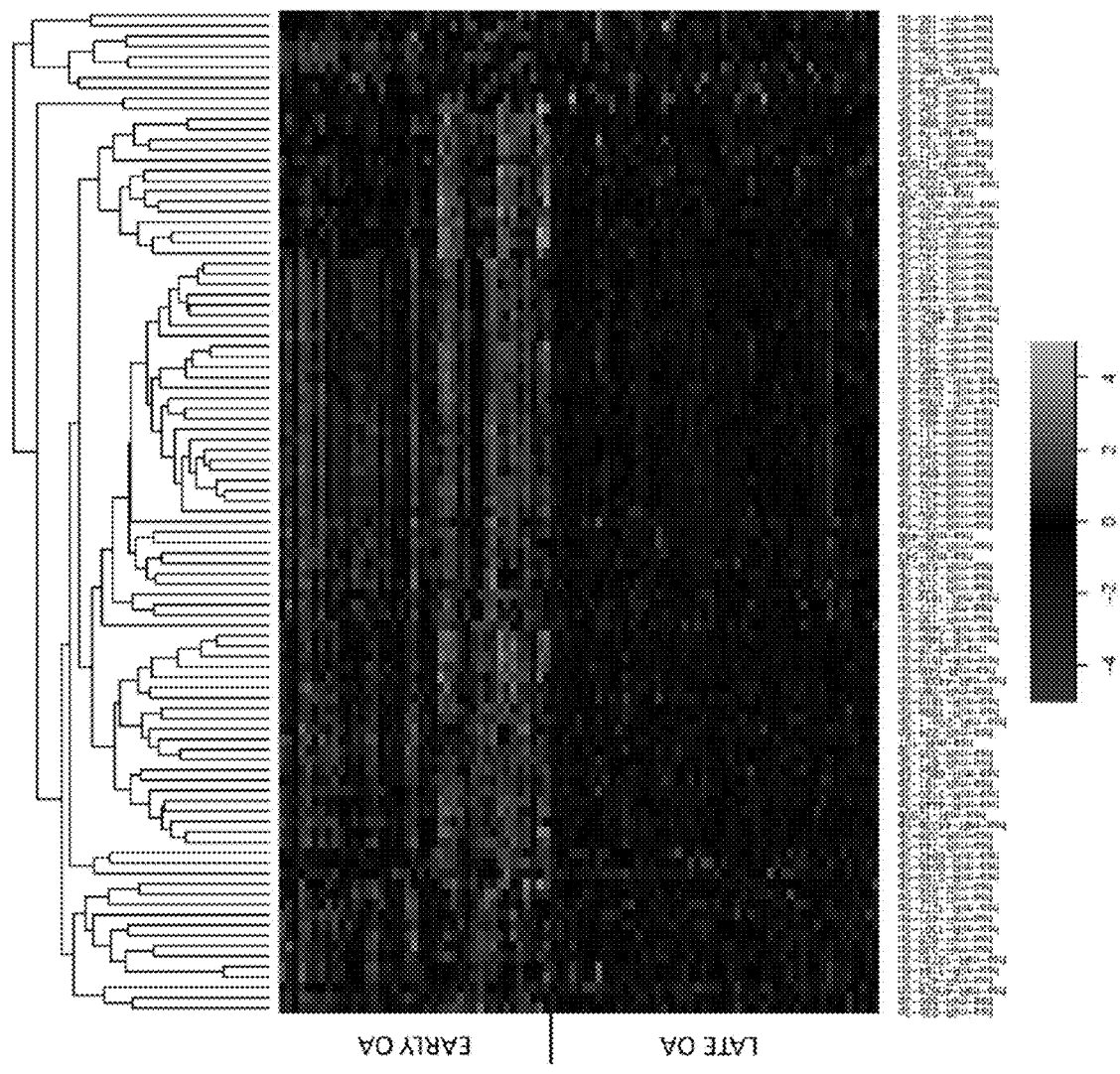
FIG. 3 shows differentially expressed microRNAs in early OA plasma as compared to late OA plasma. (A) Heatmap showing log fold change in expression of 215 microRNAs with FDR<0.01 in early OA samples (n=41) as compared to late OA samples (n=50). (B) MicroRNAs (n=7) selected based on higher expression across 95% or more of samples in the early OA group as compared to the median expression in the late OA group. log FC=log fold change. log CPM=log counts-per-million. FDR=false discovery rate. (C) T-distributed stochastic neighbour embedding plot using the 7 microRNAs shown in (B; left graph) as variables to group early OA and late OA samples, as compared to 7 randomly selected microRNAs (right graph).
Figure 3:
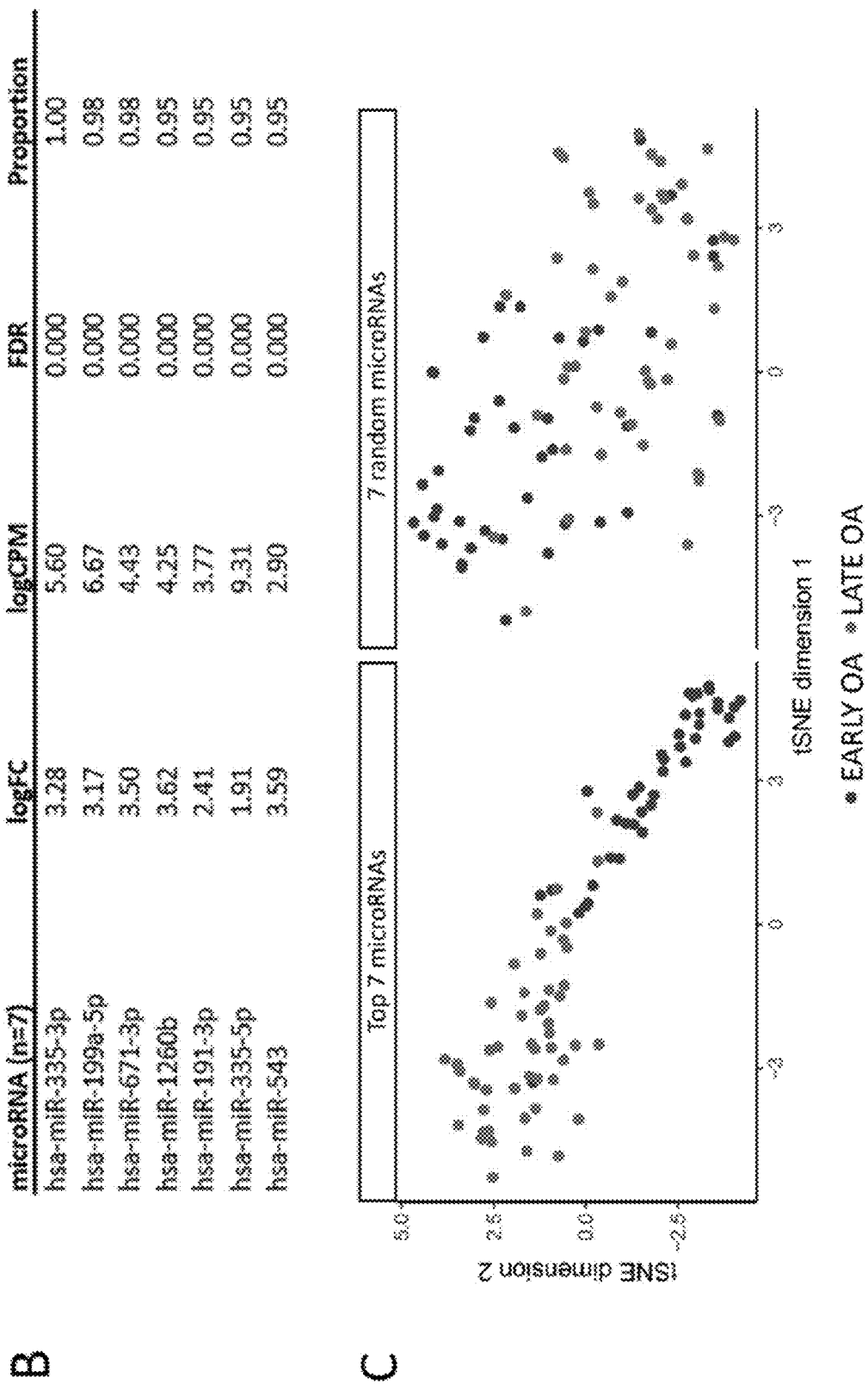

As the third step, the list of 215 microRNAs was filtered in a biologically relevant manner, selecting microRNAs expressed consistently higher or lower across samples in the early OA group as compared to the median expression level in the late OA group using progressing stringency. This filtering yielded 97 microRNAs that showed higher expression across 85% or more of samples in the early OA group as compared to the late OA group (FIG. 3A; table 2B). Among these, 7 microRNAs (hsa-miR-335-3p, hsa-miR-199a-5p, hsa-miR-671-3p, hsa-miR-1260b, hsa-miR-191-3p, hsa-miR-335-5p, and hsa-miR-543) had higher expression in 95% or more of samples in the early OA group, including hsa-miR-335-3p which was consistently elevated in 100% of early OA samples, showing a 3.28 log fold difference in early OA versus late OA (FIG. 3B). When a t-distributed stochastic neighbour embedding plot was used to visualize the early OA and late OA clusters generated using these 7 microRNAs as variables, clear separation of groups was observed (FIG. 3C).

Identifying a Panel of Novel Circulating microRNAs in Early Radiographic Knee OA Having identified a panel of 7 microRNAs in the early OA cohort, we next investigated whether there were novel microRNAs present in early OA, as discovery of novel microRNAs is a major advantage of using sequencing technology. Novel microRNAs were detected based on their predicted secondary structure and lack of homology with murine microRNAs (FIG. 5). Using progressing stringencies, this list was filtered for novel microRNA sequences that consistently appeared across samples within a cohort (early OA or late OA). Filtering for novel microRNAs that were expressed in ≥85% of samples yielded 1 novel microRNA in the early OA cohort (novel_miRNA_11) that was also found in ≥85% of samples in the late OA cohort, and 4 novel microRNAs in the late OA cohort (novel_miRNA_7, 8, 9, 11) that were also found in ≥50% of samples in the early OA cohort.

To identify novel microRNAs that were potentially associated with early OA but not late OA and vice versa, we filtered for novel microRNAs that were expressed in ≥50% of samples within a cohort. This revealed 11 novel microRNAs in the early OA cohort and 9 microRNAs in the late OA cohort, 7 of which were overlapping, leaving 4 novel microRNAs in the early OA cohort and 2 novel microRNAs in the late OA cohort (FIG. 4). The 4 novel microRNAs identified in ≥50% of samples in the early OA cohort were found in 36% or less of samples in the late OA cohort, demonstrating that these 4 novel microRNAs are more commonly found in patients with early OA than late OA (FIG. 4). Finally, the novel microRNA sequences were compared to a previous list of novel microRNAs generated from sequencing 13 different human tissue types (21). As shown in FIG. 4, the sequences for 4 of the microRNAs (novel_miRNA_3, 5, 7, 9) were previously reported, providing independent evidence of the existence of these novel microRNAs, and supporting the method we used for discovery of novel microRNAs.

Identifying a Panel of Circulating microRNAs in Late Radiographic Knee OA

Figure 8:
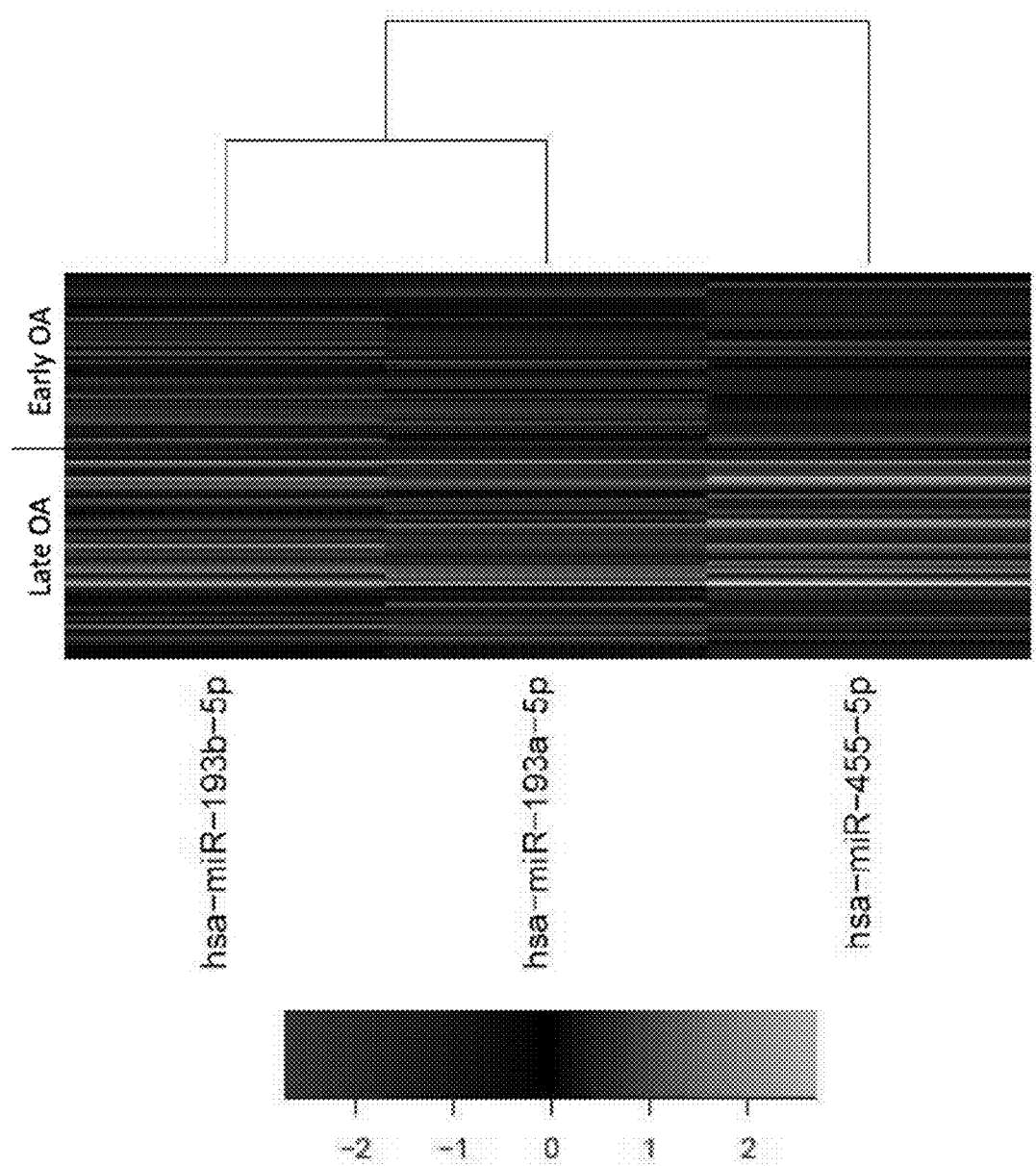
FIG. 8 shows differentially expressed microRNAs in late OA plasma as compared to early OA plasma. Heatmap and table showing log fold change in expression of 3 microRNAs with FDR<0.01 in late OA samples (n=50) as compared to early OA samples (n=41). log FC=log fold change. log CPM=log counts-per-million. FDR=false discovery rate.

To identify circulating microRNAs that were associated with late OA, the list of 215 differentially expressed microRNAs was filtered for microRNAs which were consistently higher or lower in expression across samples in the late OA group, as compared to the median expression level in the early OA group. Filtering for microRNAs that were expressed in ≥85% of samples in the late OA group yielded no microRNAs, but filtering at a minimum threshold of 50% yielded 3 microRNAs (table 2C). The 3 microRNAs showed increased expression in late OA as compared to early OA, with hsa-miR-193b-5p, hsa-miR-193a-5p, and hsa-miR-455-5p showing higher expression in 62%, 52%, and 50% of late OA samples, respectively (FIG. 8). Characterizing novel microRNAs, novel_miRNA_5 and 6 were identified in 50% of late OA samples, with novel_miRNA_5 being previously described (21). Because novel_miRNA_6 was also present in 44% of samples in the early OA cohort, it is unlikely to be unique to late OA samples (FIG. 4). Since a larger and more consistently expressed panel of microRNAs was identified in early OA samples, subsequent analyses focused on early OA samples.

TABLE 2A (Total N = 417)

| miRNA (n = 417) | logFC | logCPM | F | PValue | FDR |
|---|---|---|---|---|---|
| hsa-miR-107 | 4.35 | 4.97 | 84.68 | 0.00 | 0.00 |
| hsa-miR-4433b-5p | 4.28 | 6.14 | 78.79 | 0.00 | 0.00 |
| hsa-miR-379-5p | 4.34 | 6.85 | 70.85 | 0.00 | 0.00 |
| hsa-miR-654-3p | 4.38 | 6.75 | 70.24 | 0.00 | 0.00 |
| hsa-miR-431-5p | 4.76 | 7.47 | 70.01 | 0.00 | 0.00 |
| hsa-miR-411-5p | 4.79 | 4.84 | 69.45 | 0.00 | 0.00 |
| hsa-miR-671-3p | 3.50 | 4.43 | 69.02 | 0.00 | 0.00 |
| hsa-miR-496 | 4.57 | 1.88 | 68.51 | 0.00 | 0.00 |
| hsa-miR-335-3p | 3.28 | 5.60 | 67.54 | 0.00 | 0.00 |
| hsa-miR-744-5p | 3.27 | 8.97 | 67.14 | 0.00 | 0.00 |
| hsa-miR-1260b | 3.62 | 4.25 | 65.49 | 0.00 | 0.00 |
| hsa-miR-548j-5p | 3.42 | 5.16 | 65.07 | 0.00 | 0.00 |
| hsa-miR-127-3p | 4.70 | 5.86 | 64.19 | 0.00 | 0.00 |
| hsa-miR-136-5p | 4.14 | 3.73 | 62.84 | 0.00 | 0.00 |
| hsa-miR-487b-3p | 4.65 | 5.09 | 62.34 | 0.00 | 0.00 |
| hsa-miR-432-5p | 4.39 | 8.92 | 62.12 | 0.00 | 0.00 |
| hsa-miR-376c-3p | 4.30 | 5.08 | 61.52 | 0.00 | 0.00 |
| hsa-miR-199a-5p | 3.17 | 6.67 | 60.76 | 0.00 | 0.00 |
| hsa-miR-889-3p | 4.52 | 4.12 | 60.30 | 0.00 | 0.00 |
| hsa-miR-485-3p | 4.22 | 6.62 | 60.27 | 0.00 | 0.00 |
| hsa-miR-381-3p | 4.36 | 6.06 | 58.84 | 0.00 | 0.00 |
| hsa-miR-26a-1-3p | 3.67 | 3.69 | 58.70 | 0.00 | 0.00 |
| hsa-miR-493-5p | 4.30 | 5.35 | 58.28 | 0.00 | 0.00 |
| hsa-miR-1273h-3p | 3.48 | 3.36 | 57.88 | 0.00 | 0.00 |
| hsa-miR-374b-5p | 2.09 | 6.52 | 57.77 | 0.00 | 0.00 |
| hsa-miR-127-5p | 4.58 | 1.73 | 57.59 | 0.00 | 0.00 |
| hsa-miR-370-3p | 4.83 | 5.26 | 57.44 | 0.00 | 0.00 |
| hsa-miR-376a-3p | 4.42 | 3.42 | 56.84 | 0.00 | 0.00 |
| hsa-miR-494-3p | 3.77 | 4.76 | 56.83 | 0.00 | 0.00 |
| hsa-miR-495-3p | 4.40 | 2.77 | 56.68 | 0.00 | 0.00 |
| hsa-miR-409-3p | 4.09 | 8.81 | 56.26 | 0.00 | 0.00 |
| hsa-miR-28-3p | 2.66 | 8.31 | 56.02 | 0.00 | 0.00 |
| hsa-let-7e-5p | 2.49 | 9.08 | 55.76 | 0.00 | 0.00 |
| hsa-miR-3120-3p | 4.06 | 2.02 | 55.50 | 0.00 | 0.00 |
| hsa-miR-1185-1-3p | 5.22 | 2.53 | 54.49 | 0.00 | 0.00 |
| hsa-miR-181c-3p | 3.20 | 3.60 | 54.33 | 0.00 | 0.00 |
| hsa-miR-766-3p | 4.44 | 4.44 | 54.00 | 0.00 | 0.00 |
| hsa-miR-151a-3p | 2.46 | 10.69 | 53.98 | 0.00 | 0.00 |
| hsa-miR-369-5p | 3.78 | 5.64 | 53.75 | 0.00 | 0.00 |
| hsa-miR-376b-3p | 4.71 | 2.00 | 52.56 | 0.00 | 0.00 |
| hsa-miR-223-3p | 2.09 | 14.35 | 52.42 | 0.00 | 0.00 |
| hsa-miR-409-5p | 4.05 | 3.03 | 52.41 | 0.00 | 0.00 |
| hsa-miR-30e-3p | 1.77 | 7.42 | 52.27 | 0.00 | 0.00 |
| hsa-miR-543 | 3.59 | 2.90 | 51.76 | 0.00 | 0.00 |
| hsa-miR-28-5p | 3.21 | 4.25 | 51.59 | 0.00 | 0.00 |
| hsa-miR-3617-5p | 4.40 | 1.07 | 50.91 | 0.00 | 0.00 |
| hsa-miR-23b-3p | 1.79 | 10.21 | 50.70 | 0.00 | 0.00 |
| hsa-miR-339-5p | 2.62 | 7.33 | 50.25 | 0.00 | 0.00 |
| hsa-miR-556-3p | 3.47 | 2.90 | 50.19 | 0.00 | 0.00 |
| hsa-miR-323a-3p | 3.44 | 4.65 | 49.35 | 0.00 | 0.00 |
| hsa-miR-379-3p | 4.55 | 1.56 | 48.49 | 0.00 | 0.00 |
| hsa-miR-329-3p | 4.16 | 3.06 | 48.41 | 0.00 | 0.00 |
| hsa-miR-493-3p | 4.44 | 4.40 | 48.14 | 0.00 | 0.00 |
| hsa-miR-337-5p | 3.46 | 4.39 | 47.98 | 0.00 | 0.00 |
| hsa-miR-431-3p | 4.29 | 1.47 | 47.96 | 0.00 | 0.00 |
| hsa-miR-146a-5p | 2.53 | 13.34 | 47.86 | 0.00 | 0.00 |
| hsa-miR-382-3p | 3.80 | 3.84 | 47.85 | 0.00 | 0.00 |
| hsa-miR-539-3p | 4.46 | 2.51 | 47.65 | 0.00 | 0.00 |
| hsa-miR-548a-3p | 3.36 | 2.71 | 46.11 | 0.00 | 0.00 |
| hsa-miR-126-3p | 1.76 | 14.49 | 45.62 | 0.00 | 0.00 |
| hsa-miR-99b-5p | 2.12 | 8.15 | 45.53 | 0.00 | 0.00 |
| hsa-miR-6852-5p | 4.05 | 2.84 | 45.19 | 0.00 | 0.00 |
| hsa-miR-3184-5p | 1.93 | 8.05 | 45.17 | 0.00 | 0.00 |
| hsa-miR-154-5p | 4.10 | 2.59 | 44.55 | 0.00 | 0.00 |
| hsa-miR-628-5p | 2.50 | 5.01 | 44.39 | 0.00 | 0.00 |
| hsa-miR-548ax | 3.75 | 1.71 | 44.26 | 0.00 | 0.00 |
| hsa-miR-485-5p | 3.29 | 4.54 | 44.24 | 0.00 | 0.00 |
| hsa-miR-4446-3p | 4.05 | 3.29 | 44.20 | 0.00 | 0.00 |
| hsa-miR-331-3p | 2.22 | 4.12 | 43.86 | 0.00 | 0.00 |
| hsa-miR-181d-5p | 2.60 | 4.40 | 43.71 | 0.00 | 0.00 |
| hsa-miR-491-5p | 2.46 | 3.45 | 43.45 | 0.00 | 0.00 |
| hsa-miR-423-3p | 1.84 | 9.76 | 43.27 | 0.00 | 0.00 |
| hsa-miR-487b-5p | 4.38 | 1.56 | 43.22 | 0.00 | 0.00 |
| hsa-miR-299-5p | 4.07 | 2.11 | 43.13 | 0.00 | 0.00 |
| hsa-miR-369-3p | 3.69 | 6.45 | 42.97 | 0.00 | 0.00 |
| hsa-miR-625-5p | 2.49 | 5.36 | 42.66 | 0.00 | 0.00 |
| hsa-miR-142-3p | 2.52 | 13.45 | 42.29 | 0.00 | 0.00 |
| hsa-miR-328-3p | 2.17 | 7.97 | 42.27 | 0.00 | 0.00 |
| hsa-miR-323b-3p | 3.66 | 5.59 | 41.74 | 0.00 | 0.00 |
| hsa-miR-1301-3p | 2.40 | 3.79 | 41.60 | 0.00 | 0.00 |
| hsa-miR-340-5p | 2.01 | 8.25 | 41.24 | 0.00 | 0.00 |
| hsa-miR-134-5p | 3.61 | 7.61 | 41.22 | 0.00 | 0.00 |
| hsa-miR-181a-3p | 2.18 | 4.51 | 41.02 | 0.00 | 0.00 |
| hsa-miR-377-3p | 3.12 | 3.40 | 40.96 | 0.00 | 0.00 |
| hsa-miR-146b-5p | 1.89 | 8.68 | 40.87 | 0.00 | 0.00 |
| hsa-miR-625-3p | 2.11 | 8.35 | 39.60 | 0.00 | 0.00 |
| hsa-miR-3074-5p | 1.61 | 9.33 | 39.41 | 0.00 | 0.00 |
| hsa-miR-26a-5p | 1.42 | 13.74 | 39.29 | 0.00 | 0.00 |
| hsa-miR-590-3p | 1.64 | 5.84 | 38.84 | 0.00 | 0.00 |
| hsa-miR-136-3p | 2.95 | 3.98 | 38.77 | 0.00 | 0.00 |
| hsa-miR-4433b-3p | 4.29 | 2.90 | 38.12 | 0.00 | 0.00 |
| hsa-miR-223-5p | 1.77 | 8.16 | 36.96 | 0.00 | 0.00 |
| hsa-miR-130b-5p | 1.82 | 4.44 | 36.93 | 0.00 | 0.00 |
| hsa-miR-425-3p | 2.20 | 5.28 | 36.82 | 0.00 | 0.00 |
| hsa-miR-382-5p | 3.18 | 9.00 | 36.53 | 0.00 | 0.00 |
| hsa-miR-412-5p | 4.23 | 1.99 | 36.37 | 0.00 | 0.00 |
| hsa-miR-126-5p | 1.27 | 12.55 | 36.27 | 0.00 | 0.00 |
| hsa-miR-1277-5p | 2.13 | 5.72 | 36.26 | 0.00 | 0.00 |
| hsa-miR-551b-3p | 3.61 | 1.43 | 36.21 | 0.00 | 0.00 |
| hsa-miR-337-3p | 3.32 | 2.21 | 35.79 | 0.00 | 0.00 |
| hsa-miR-24-3p | 1.38 | 10.82 | 35.08 | 0.00 | 0.00 |
| hsa-miR-1260a | 2.07 | 3.55 | 34.99 | 0.00 | 0.00 |
| hsa-miR-191-5p | 1.28 | 12.27 | 34.67 | 0.00 | 0.00 |
| hsa-miR-30b-5p | 1.63 | 6.50 | 34.09 | 0.00 | 0.00 |
| hsa-miR-9-5p | 1.92 | 2.68 | 34.03 | 0.00 | 0.00 |
| hsa-miR-191-3p | 2.41 | 3.77 | 33.30 | 0.00 | 0.00 |
| hsa-miR-301a-5p | 2.89 | 2.06 | 33.18 | 0.00 | 0.00 |
| hsa-miR-26b-3p | 1.46 | 4.33 | 32.44 | 0.00 | 0.00 |
| hsa-miR-1250-5p | 3.19 | 1.34 | 32.16 | 0.00 | 0.00 |
| hsa-miR-335-5p | 1.91 | 9.31 | 31.92 | 0.00 | 0.00 |
| hsa-miR-584-5p | 1.92 | 9.61 | 31.90 | 0.00 | 0.00 |
| hsa-miR-103a-3p | 1.17 | 13.11 | 31.49 | 0.00 | 0.00 |
| hsa-miR-181c-5p | 1.99 | 3.27 | 31.39 | 0.00 | 0.00 |
| hsa-miR-224-5p | 2.84 | 7.75 | 31.38 | 0.00 | 0.00 |
| hsa-miR-148b-3p | 1.26 | 10.66 | 31.00 | 0.00 | 0.00 |
| hsa-miR-5189-5p | 2.84 | 1.79 | 30.57 | 0.00 | 0.00 |
| hsa-miR-22-5p | 1.36 | 4.32 | 30.34 | 0.00 | 0.00 |
| hsa-miR-151a-5p | 1.63 | 6.75 | 30.18 | 0.00 | 0.00 |
| hsa-miR-1296-5p | 2.80 | 2.40 | 29.92 | 0.00 | 0.00 |
| hsa-miR-769-5p | 1.71 | 4.25 | 29.08 | 0.00 | 0.00 |
| hsa-miR-197-3p | 1.38 | 7.25 | 29.00 | 0.00 | 0.00 |
| hsa-miR-6813-5p | 3.16 | 1.09 | 28.18 | 0.00 | 0.00 |
| hsa-miR-99b-3p | 2.45 | 2.97 | 27.79 | 0.00 | 0.00 |
| hsa-miR-128-3p | 0.98 | 9.68 | 27.67 | 0.00 | 0.00 |
| hsa-miR-2355-3p | 2.43 | 3.35 | 26.76 | 0.00 | 0.00 |
| hsa-miR-221-3p | 1.53 | 11.34 | 25.99 | 0.00 | 0.00 |
| hsa-miR-181a-2-3p | 1.11 | 5.59 | 25.55 | 0.00 | 0.00 |
| hsa-miR-1-3p | 2.55 | 6.80 | 25.41 | 0.00 | 0.00 |
| hsa-miR-656-3p | 3.23 | 1.29 | 25.35 | 0.00 | 0.00 |
| hsa-miR-326 | 2.33 | 1.96 | 24.90 | 0.00 | 0.00 |
| hsa-miR-548e-3p | 1.73 | 3.23 | 24.36 | 0.00 | 0.00 |
| hsa-miR-455-5p | −2.74 | 1.44 | 24.35 | 0.00 | 0.00 |
| hsa-miR-5187-5p | 2.54 | 3.06 | 23.46 | 0.00 | 0.00 |
| hsa-miR-7-1-3p | 1.57 | 2.98 | 23.24 | 0.00 | 0.00 |
| hsa-miR-361-5p | 1.01 | 8.60 | 23.11 | 0.00 | 0.00 |
| hsa-miR-338-3p | 1.49 | 3.98 | 22.79 | 0.00 | 0.00 |
| hsa-miR-6842-3p | 1.94 | 2.96 | 22.54 | 0.00 | 0.00 |
| hsa-miR-140-3p | 0.82 | 9.75 | 22.45 | 0.00 | 0.00 |
| hsa-let-7f-5p | 0.97 | 14.79 | 22.30 | 0.00 | 0.00 |
| hsa-miR-33a-5p | 1.98 | 3.11 | 22.18 | 0.00 | 0.00 |
| hsa-miR-181a-5p | 0.99 | 10.23 | 21.99 | 0.00 | 0.00 |
| hsa-miR-27a-3p | 1.06 | 8.96 | 21.85 | 0.00 | 0.00 |
| hsa-miR-139-3p | 1.85 | 6.11 | 21.64 | 0.00 | 0.00 |
| hsa-miR-3177-3p | 2.13 | 1.98 | 21.45 | 0.00 | 0.00 |
| hsa-miR-133a-3p | 2.43 | 5.08 | 21.41 | 0.00 | 0.00 |
| hsa-miR-374b-3p | 2.08 | 1.89 | 21.41 | 0.00 | 0.00 |
| hsa-miR-1277-3p | 1.94 | 2.75 | 21.23 | 0.00 | 0.00 |
| hsa-miR-185-3p | 1.48 | 5.22 | 21.14 | 0.00 | 0.00 |
| hsa-miR-142-5p | 1.12 | 9.76 | 20.84 | 0.00 | 0.00 |
| hsa-miR-3679-5p | 2.26 | 4.17 | 20.60 | 0.00 | 0.00 |
| hsa-miR-11400 | 4.42 | 4.52 | 20.54 | 0.00 | 0.00 |
| hsa-miR-1271-5p | 1.99 | 2.30 | 20.47 | 0.00 | 0.00 |

TABLE 2A-continued (Total N = 417)

| miRNA (n = 417) | logFC | logCPM | F | PValue | FDR |
| --- | --- | --- | --- | --- | --- |
| hsa-miR-301a-3p | 1.11 | 5.68 | 20.43 | 0.00 | 0.00 |
| hsa-miR-433-3p | 3.14 | 1.30 | 20.29 | 0.00 | 0.00 |
| hsa-miR-877-5p | 2.13 | 3.48 | 19.92 | 0.00 | 0.00 |
| hsa-miR-760 | 2.45 | 4.40 | 19.84 | 0.00 | 0.00 |
| hsa-miR-652-3p | 1.21 | 6.50 | 19.75 | 0.00 | 0.00 |
| hsa-miR-1226-3p | 1.48 | 2.95 | 18.79 | 0.00 | 0.00 |
| hsa-miR-339-3p | 1.12 | 5.51 | 18.63 | 0.00 | 0.00 |
| hsa-miR-628-3p | 1.16 | 4.29 | 18.43 | 0.00 | 0.00 |
| hsa-miR-664b-5p | 1.83 | 2.77 | 18.13 | 0.00 | 0.00 |
| hsa-miR-155-5p | 0.99 | 8.96 | 18.08 | 0.00 | 0.00 |
| hsa-miR-130a-3p | 0.86 | 7.82 | 17.84 | 0.00 | 0.00 |
| hsa-miR-21-3p | 1.75 | 2.88 | 17.28 | 0.00 | 0.00 |
| hsa-miR-20a-3p | 1.77 | 2.24 | 17.15 | 0.00 | 0.00 |
| hsa-miR-23a-3p | 0.85 | 10.49 | 16.89 | 0.00 | 0.00 |
| hsa-miR-30c-1-3p | 2.10 | 1.59 | 16.77 | 0.00 | 0.00 |
| hsa-miR-671-5p | 1.56 | 4.97 | 16.09 | 0.00 | 0.00 |
| hsa-miR-664a-3p | 1.17 | 3.55 | 15.94 | 0.00 | 0.00 |
| hsa-miR-342-3p | 0.88 | 11.15 | 15.92 | 0.00 | 0.00 |
| hsa-miR-30c-5p | 0.97 | 8.52 | 15.42 | 0.00 | 0.00 |
| hsa-miR-374a-3p | 0.97 | 4.44 | 15.30 | 0.00 | 0.00 |
| hsa-miR-664a-5p | 1.30 | 6.81 | 15.07 | 0.00 | 0.00 |
| hsa-miR-574-3p | 0.89 | 6.31 | 14.62 | 0.00 | 0.00 |
| hsa-miR-374a-5p | 0.79 | 8.84 | 13.97 | 0.00 | 0.00 |
| hsa-miR-590-5p | 1.21 | 2.75 | 13.96 | 0.00 | 0.00 |
| hsa-miR-4662a-5p | 1.50 | 2.59 | 13.61 | 0.00 | 0.00 |
| hsa-miR-4665-5p | 2.37 | 1.01 | 13.31 | 0.00 | 0.00 |
| hsa-miR-766-5p | 2.21 | 1.39 | 12.95 | 0.00 | 0.00 |
| hsa-miR-103b | 0.51 | 11.92 | 12.43 | 0.00 | 0.00 |
| hsa-miR-1179 | 1.11 | 3.31 | 12.36 | 0.00 | 0.00 |
| hsa-miR-6741-3p | 1.34 | 2.05 | 12.35 | 0.00 | 0.00 |
| hsa-miR-574-5p | 1.07 | 3.22 | 12.26 | 0.00 | 0.00 |
| hsa-miR-98-5p | 0.68 | 8.90 | 12.11 | 0.00 | 0.00 |
| hsa-miR-139-5p | 1.03 | 5.01 | 11.87 | 0.00 | 0.00 |
| hsa-miR-1306-5p | 0.66 | 6.11 | 11.77 | 0.00 | 0.00 |
| hsa-miR-152-3p | 1.00 | 6.92 | 11.75 | 0.00 | 0.00 |
| hsa-miR-27b-3p | 0.87 | 10.14 | 11.71 | 0.00 | 0.00 |
| hsa-miR-17-3p | 1.16 | 3.42 | 11.63 | 0.00 | 0.00 |
| hsa-miR-26b-5p | 0.62 | 14.00 | 11.56 | 0.00 | 0.00 |
| hsa-miR-193b-5p | −1.34 | 3.59 | 11.50 | 0.00 | 0.00 |
| hsa-miR-200c-3p | 1.02 | 5.58 | 10.98 | 0.00 | 0.00 |
| hsa-miR-182-5p | −1.06 | 10.20 | 10.95 | 0.00 | 0.00 |
| hsa-miR-1287-5p | 0.99 | 3.61 | 10.94 | 0.00 | 0.00 |
| hsa-miR-183-5p | −1.14 | 8.79 | 10.73 | 0.00 | 0.00 |
| hsa-miR-3065-5p | 1.24 | 2.90 | 10.69 | 0.00 | 0.00 |
| hsa-miR-181b-5p | 0.78 | 7.82 | 10.62 | 0.00 | 0.00 |
| hsa-miR-342-5p | 1.18 | 3.13 | 10.53 | 0.00 | 0.00 |
| hsa-miR-1249-3p | 1.61 | 2.78 | 10.43 | 0.00 | 0.00 |
| hsa-miR-193a-5p | −1.01 | 6.52 | 10.39 | 0.00 | 0.00 |
| hsa-miR-16-5p | −0.56 | 18.48 | 9.94 | 0.00 | 0.00 |
| hsa-miR-192-5p | −0.89 | 9.81 | 9.86 | 0.00 | 0.00 |
| hsa-miR-3115 | 1.93 | 1.27 | 9.78 | 0.00 | 0.00 |
| hsa-miR-146b-3p | 1.00 | 2.97 | 9.75 | 0.00 | 0.01 |
| hsa-miR-629-5p | −0.75 | 7.08 | 9.58 | 0.00 | 0.01 |
| hsa-miR-2276-3p | 1.79 | 1.31 | 9.53 | 0.00 | 0.01 |
| hsa-miR-3605-3p | −0.59 | 4.13 | 9.47 | 0.00 | 0.01 |
| hsa-miR-1307-3p | 0.72 | 5.50 | 9.21 | 0.00 | 0.01 |
| hsa-miR-598-3p | 0.62 | 5.05 | 9.20 | 0.00 | 0.01 |
| hsa-miR-18a-5p | 0.61 | 6.91 | 9.12 | 0.00 | 0.01 |
| hsa-let-7d-3p | 0.50 | 8.58 | 8.80 | 0.00 | 0.01 |
| hsa-miR-1306-3p | 0.86 | 3.65 | 8.64 | 0.00 | 0.01 |
| hsa-miR-589-5p | 0.57 | 4.02 | 8.46 | 0.00 | 0.01 |
| hsa-miR-345-5p | 0.65 | 5.00 | 8.45 | 0.00 | 0.01 |
| hsa-miR-7976 | −1.07 | 2.27 | 8.38 | 0.00 | 0.01 |
| hsa-miR-362-5p | 1.12 | 2.60 | 8.20 | 0.01 | 0.01 |
| hsa-miR-125b-5p | −0.76 | 9.10 | 8.18 | 0.01 | 0.01 |
| hsa-miR-421 | 0.47 | 6.28 | 7.93 | 0.01 | 0.01 |
| hsa-miR-23b-5p | 1.17 | 3.28 | 7.81 | 0.01 | 0.01 |
| hsa-miR-1224-5p | −1.02 | 2.83 | 7.76 | 0.01 | 0.01 |
| hsa-let-7i-5p | 0.43 | 14.60 | 7.75 | 0.01 | 0.01 |
| hsa-miR-30d-3p | 0.97 | 2.35 | 7.71 | 0.01 | 0.01 |
| hsa-miR-636 | −1.03 | 3.42 | 7.71 | 0.01 | 0.01 |
| hsa-miR-1908-5p | 0.91 | 5.04 | 7.55 | 0.01 | 0.01 |
| hsa-miR-324-3p | 0.56 | 4.79 | 7.41 | 0.01 | 0.01 |
| hsa-miR-30e-5p | 0.38 | 12.51 | 7.40 | 0.01 | 0.01 |
| hsa-miR-454-5p | 0.55 | 5.13 | 7.29 | 0.01 | 0.02 |
| hsa-miR-885-3p | −1.52 | 2.80 | 7.10 | 0.01 | 0.02 |
| hsa-miR-23a-5p | 1.63 | 1.16 | 7.03 | 0.01 | 0.02 |
| hsa-miR-20a-5p | 0.43 | 10.70 | 6.95 | 0.01 | 0.02 |
| hsa-miR-21-5p | 0.50 | 14.75 | 6.83 | 0.01 | 0.02 |
| hsa-miR-194-5p | −0.69 | 9.40 | 6.80 | 0.01 | 0.02 |
| hsa-miR-16-2-3p | −0.54 | 6.83 | 6.77 | 0.01 | 0.02 |
| hsa-miR-29c-5p | 0.54 | 4.60 | 6.67 | 0.01 | 0.02 |
| hsa-miR-1294 | −0.72 | 5.42 | 6.66 | 0.01 | 0.02 |
| hsa-miR-3613-5p | −0.84 | 9.39 | 6.62 | 0.01 | 0.02 |
| hsa-miR-500a-3p | 0.60 | 3.84 | 6.37 | 0.01 | 0.02 |
| hsa-miR-4732-5p | −0.71 | 7.18 | 6.11 | 0.02 | 0.03 |
| hsa-miR-532-3p | −0.47 | 6.15 | 5.78 | 0.02 | 0.03 |
| hsa-miR-6721-5p | 1.11 | 1.98 | 5.62 | 0.02 | 0.03 |
| hsa-miR-17-5p | 0.36 | 8.83 | 5.58 | 0.02 | 0.04 |
| hsa-miR-146a-3p | 2.16 | 2.55 | 5.58 | 0.02 | 0.04 |
| hsa-miR-122-5p | −1.04 | 14.11 | 5.55 | 0.02 | 0.04 |
| hsa-miR-132-3p | 0.52 | 4.71 | 5.46 | 0.02 | 0.04 |
| hsa-miR-15a-5p | −0.47 | 10.26 | 5.39 | 0.02 | 0.04 |
| hsa-miR-29c-3p | −0.53 | 9.97 | 5.31 | 0.02 | 0.04 |
| hsa-miR-1255b-5p | −0.62 | 4.94 | 4.96 | 0.03 | 0.05 |
| hsa-miR-3688-3p | −0.56 | 3.70 | 4.90 | 0.03 | 0.05 |
| hsa-miR-196b-5p | −0.46 | 7.58 | 4.90 | 0.03 | 0.05 |
| hsa-miR-122b-3p | −1.00 | 12.01 | 4.80 | 0.03 | 0.05 |
| hsa-miR-3940-3p | −0.94 | 2.60 | 4.68 | 0.03 | 0.06 |
| hsa-miR-216a-5p | −1.58 | 1.23 | 4.64 | 0.03 | 0.06 |
| hsa-miR-135a-5p | 0.84 | 2.40 | 4.60 | 0.03 | 0.06 |
| hsa-miR-125b-2-3p | −0.78 | 2.89 | 4.51 | 0.04 | 0.06 |
| hsa-miR-125a-3p | 1.12 | 2.41 | 4.50 | 0.04 | 0.06 |
| hsa-miR-4732-3p | −0.76 | 6.64 | 4.48 | 0.04 | 0.06 |
| hsa-let-7b-5p | −0.33 | 15.53 | 4.40 | 0.04 | 0.06 |
| hsa-miR-3143 | −0.54 | 3.21 | 4.40 | 0.04 | 0.06 |
| hsa-miR-941 | 0.60 | 5.37 | 4.34 | 0.04 | 0.06 |
| hsa-miR-4685-3p | −0.77 | 2.47 | 4.34 | 0.04 | 0.06 |
| hsa-miR-484 | −0.36 | 10.75 | 4.29 | 0.04 | 0.07 |
| hsa-miR-548l | 0.54 | 2.94 | 4.22 | 0.04 | 0.07 |
| hsa-miR-34a-5p | −0.69 | 5.47 | 4.15 | 0.04 | 0.07 |
| hsa-miR-122-3p | −1.20 | 2.36 | 4.15 | 0.04 | 0.07 |
| hsa-let-7c-5p | −0.67 | 9.04 | 3.98 | 0.05 | 0.08 |
| hsa-miR-1180-5p | −0.51 | 6.26 | 3.96 | 0.05 | 0.08 |
| hsa-miR-885-5p | −0.98 | 3.50 | 3.94 | 0.05 | 0.08 |
| hsa-miR-548n | 0.80 | 1.89 | 3.86 | 0.05 | 0.08 |
| hsa-miR-4326 | 1.12 | 3.25 | 3.83 | 0.05 | 0.08 |
| hsa-miR-483-5p | −0.78 | 6.65 | 3.83 | 0.05 | 0.08 |
| hsa-miR-32-5p | −0.41 | 9.65 | 3.79 | 0.05 | 0.08 |
| hsa-miR-218-5p | −1.95 | 3.25 | 3.74 | 0.06 | 0.09 |
| hsa-miR-1255a | 0.92 | 1.85 | 3.63 | 0.06 | 0.09 |
| hsa-miR-96-5p | −0.65 | 6.60 | 3.62 | 0.06 | 0.09 |
| hsa-miR-185-5p | 0.30 | 11.30 | 3.62 | 0.06 | 0.09 |
| hsa-miR-149-5p | −1.08 | 1.78 | 3.57 | 0.06 | 0.09 |
| hsa-miR-6862-5p | 1.11 | 1.10 | 3.56 | 0.06 | 0.09 |
| hsa-miR-4742-5p | −0.49 | 3.33 | 3.52 | 0.06 | 0.10 |
| hsa-miR-92b-3p | −0.43 | 6.91 | 3.35 | 0.07 | 0.11 |
| hsa-miR-3913-5p | 0.40 | 3.11 | 3.81 | 0.07 | 0.11 |
| hsa-miR-486-5p | −0.44 | 16.45 | 3.24 | 0.08 | 0.11 |
| hsa-miR-106b-5p | −0.33 | 6.31 | 3.18 | 0.08 | 0.12 |
| hsa-miR-9-3p | 0.73 | 2.60 | 3.14 | 0.08 | 0.12 |
| hsa-miR-122b-5p | −1.15 | 1.16 | 3.11 | 0.08 | 0.12 |
| hsa-miR-7-5p | −0.34 | 8.75 | 3.07 | 0.08 | 0.12 |
| hsa-miR-3158-3p | −0.65 | 4.04 | 2.99 | 0.09 | 0.13 |
| hsa-miR-542-5p | 0.52 | 3.92 | 2.92 | 0.09 | 0.13 |
| hsa-miR-25-3p | −0.27 | 13.18 | 2.87 | 0.09 | 0.14 |
| hsa-miR-30a-5p | −0.50 | 7.75 | 2.86 | 0.09 | 0.14 |
| hsa-miR-15b-5p | −0.23 | 11.08 | 2.83 | 0.10 | 0.14 |
| hsa-miR-92b-5p | −0.48 | 3.69 | 2.82 | 0.10 | 0.14 |
| hsa-miR-143-5p | 0.73 | 3.33 | 2.82 | 0.10 | 0.14 |
| hsa-miR-483-3p | −0.85 | 3.35 | 2.79 | 0.10 | 0.14 |
| hsa-miR-3184-3p | 0.47 | 10.32 | 2.73 | 0.10 | 0.14 |
| hsa-let-7d-5p | 0.22 | 11.51 | 2.63 | 0.11 | 0.15 |
| hsa-miR-148a-5p | 0.63 | 2.58 | 2.63 | 0.11 | 0.15 |
| hsa-let-7a-3p | −0.46 | 3.54 | 2.61 | 0.11 | 0.15 |
| hsa-miR-95-3p | −0.49 | 3.92 | 2.46 | 0.12 | 0.17 |
| hsa-miR-576-5p | −0.29 | 8.25 | 2.39 | 0.13 | 0.18 |
| hsa-miR-5189-3p | 0.84 | 2.83 | 2.34 | 0.13 | 0.18 |
| hsa-let-7a-5p | 0.22 | 15.28 | 2.31 | 0.13 | 0.18 |
| hsa-miR-497-5p | 0.57 | 2.39 | 2.30 | 0.13 | 0.18 |
| hsa-let-7b-3p | −0.36 | 4.29 | 2.30 | 0.13 | 0.18 |
| hsa-miR-3200-3p | −0.56 | 3.19 | 2.28 | 0.14 | 0.18 |

TABLE 2A-continued (Total N = 417)

| miRNA (n = 417) | logFC | logCPM | F | PValue | FDR |
|---|---|---|---|---|---|
| hsa-miR-363-3p | −0.36 | 9.90 | 2.27 | 0.14 | 0.18 |
| hsa-miR-106b-3p | 0.29 | 8.16 | 2.12 | 0.15 | 0.20 |
| hsa-miR-1299 | 1.10 | 2.91 | 2.04 | 0.16 | 0.21 |
| hsa-miR-486-3p | −0.34 | 14.72 | 2.03 | 0.16 | 0.21 |
| hsa-miR-10b-5p | −0.45 | 9.70 | 2.02 | 0.16 | 0.21 |
| hsa-miR-5001-3p | −0.67 | 2.10 | 2.00 | 0.16 | 0.22 |
| hsa-miR-6877-5p | 0.63 | 1.71 | 2.00 | 0.16 | 0.22 |
| hsa-miR-1270 | 0.42 | 2.87 | 1.97 | 0.16 | 0.22 |
| hsa-miR-505-5p | −0.36 | 3.48 | 1.84 | 0.18 | 0.24 |
| hsa-miR-205-5p | −0.56 | 5.84 | 1.84 | 0.18 | 0.24 |
| hsa-miR-1285-3p | −0.41 | 2.50 | 1.76 | 0.19 | 0.25 |
| hsa-miR-505-3p | −0.37 | 3.56 | 1.75 | 0.19 | 0.25 |
| hsa-miR-10527-5p | −0.28 | 3.88 | 1.65 | 0.20 | 0.27 |
| hsa-miR-548k | 0.48 | 2.38 | 1.64 | 0.20 | 0.27 |
| hsa-miR-7706 | −0.30 | 3.28 | 1.59 | 0.21 | 0.27 |
| hsa-miR-320b | 0.33 | 8.50 | 1.58 | 0.21 | 0.28 |
| hsa-miR-10a-3p | 0.52 | 2.49 | 1.58 | 0.21 | 0.28 |
| hsa-miR-3615 | −0.18 | 8.38 | 1.55 | 0.22 | 0.28 |
| hsa-miR-195-5p | −0.29 | 5.39 | 1.53 | 0.22 | 0.28 |
| hsa-miR-660-5p | −0.20 | 7.69 | 1.51 | 0.22 | 0.29 |
| hsa-miR-99a-5p | −0.38 | 7.26 | 1.50 | 0.22 | 0.29 |
| hsa-miR-92a-3p | −0.19 | 15.31 | 1.49 | 0.23 | 0.29 |
| hsa-miR-186-5p | −0.19 | 9.85 | 1.47 | 0.23 | 0.29 |
| hsa-miR-19a-3p | 0.20 | 8.39 | 1.47 | 0.23 | 0.29 |
| hsa-miR-204-5p | −0.53 | 2.52 | 1.46 | 0.23 | 0.29 |
| hsa-miR-19b-3p | 0.19 | 10.29 | 1.44 | 0.23 | 0.29 |
| hsa-miR-296-5p | −0.35 | 4.07 | 1.39 | 0.24 | 0.30 |
| hsa-miR-1246 | −0.56 | 2.41 | 1.35 | 0.25 | 0.31 |
| hsa-miR-10a-5p | 0.27 | 9.33 | 1.35 | 0.25 | 0.31 |
| hsa-miR-2110 | −0.25 | 4.57 | 1.35 | 0.25 | 0.31 |
| hsa-miR-361-3p | 0.24 | 6.17 | 1.32 | 0.25 | 0.31 |
| hsa-miR-148a-3p | −0.17 | 11.82 | 1.31 | 0.26 | 0.32 |
| hsa-miR-148b-5p | 0.28 | 4.65 | 1.24 | 0.27 | 0.33 |
| hsa-miR-150-3p | −0.49 | 2.30 | 1.22 | 0.27 | 0.34 |
| hsa-miR-101-3p | −0.17 | 12.82 | 1.22 | 0.27 | 0.34 |
| hsa-miR-29a-3p | −0.26 | 9.21 | 1.22 | 0.27 | 0.34 |
| hsa-miR-100-5p | −0.38 | 6.02 | 1.20 | 0.28 | 0.34 |
| hsa-miR-143-3p | 0.38 | 10.46 | 1.20 | 0.28 | 0.34 |
| hsa-miR-190a-5p | 0.30 | 8.38 | 1.19 | 0.28 | 0.34 |
| hsa-miR-1307-5p | 0.47 | 3.86 | 1.16 | 0.28 | 0.34 |
| hsa-miR-93-5p | 0.19 | 12.79 | 1.13 | 0.29 | 0.35 |
| hsa-miR-4772-3p | −0.69 | 1.49 | 1.09 | 0.30 | 0.36 |
| hsa-miR-125a-5p | 0.30 | 10.70 | 1.08 | 0.30 | 0.36 |
| hsa-miR-30a-3p | −0.24 | 4.36 | 1.04 | 0.31 | 0.37 |
| hsa-miR-197-5p | −0.49 | 1.92 | 1.04 | 0.31 | 0.37 |
| hsa-miR-145-5p | 0.30 | 6.22 | 1.02 | 0.32 | 0.37 |
| hsa-let-7i-3p | −0.31 | 3.44 | 1.02 | 0.32 | 0.37 |
| hsa-miR-324-5p | −0.20 | 6.42 | 1.02 | 0.32 | 0.37 |
| hsa-miR-144-5p | −0.36 | 6.70 | 1.01 | 0.32 | 0.37 |
| hsa-miR-210-3p | −0.30 | 3.39 | 1.01 | 0.32 | 0.38 |
| hsa-miR-144-3p | −0.35 | 10.37 | 1.00 | 0.32 | 0.38 |
| hsa-miR-3187-3p | 0.40 | 2.68 | 1.00 | 0.32 | 0.38 |
| hsa-miR-320c | 0.41 | 3.44 | 0.96 | 0.33 | 0.39 |
| hsa-miR-30d-5p | −0.14 | 11.21 | 0.95 | 0.33 | 0.39 |
| hsa-miR-3200-5p | −0.45 | 2.82 | 0.95 | 0.33 | 0.39 |
| hsa-miR-375-3p | −0.44 | 7.39 | 0.89 | 0.35 | 0.40 |
| hsa-miR-199b-5p | 0.31 | 3.36 | 0.82 | 0.37 | 0.42 |
| hsa-miR-450b-5p | 0.23 | 4.04 | 0.76 | 0.39 | 0.44 |
| hsa-miR-454-5p | −0.20 | 8.67 | 0.73 | 0.40 | 0.46 |
| hsa-miR-451a | −0.27 | 15.19 | 0.71 | 0.40 | 0.46 |
| hsa-miR-140-5p | 0.19 | 7.13 | 0.71 | 0.40 | 0.46 |
| hsa-miR-503-5p | 0.31 | 3.50 | 0.68 | 0.41 | 0.47 |
| hsa-miR-320a-3p | 0.21 | 10.63 | 0.65 | 0.42 | 0.48 |
| hsa-miR-378a-3p | −0.18 | 7.57 | 0.62 | 0.43 | 0.49 |
| hsa-miR-222-3p | 0.15 | 7.50 | 0.61 | 0.44 | 0.49 |
| hsa-miR-874-3p | −0.23 | 2.99 | 0.57 | 0.45 | 0.51 |
| hsa-miR-93-3p | 0.19 | 4.58 | 0.55 | 0.46 | 0.52 |
| hsa-miR-10b-3p | −0.26 | 3.10 | 0.46 | 0.50 | 0.56 |
| hsa-miR-190b-5p | −0.12 | 4.95 | 0.43 | 0.51 | 0.57 |
| hsa-miR-499a-5p | 0.31 | 3.27 | 0.39 | 0.53 | 0.59 |
| hsa-miR-206 | −0.40 | 5.85 | 0.36 | 0.55 | 0.61 |
| hsa-miR-320d | −0.23 | 2.95 | 0.35 | 0.55 | 0.62 |
| hsa-miR-15b-3p | 0.10 | 7.53 | 0.34 | 0.56 | 0.62 |
| hsa-miR-130b-3p | 0.12 | 5.89 | 0.33 | 0.57 | 0.63 |
| hsa-miR-627-5p | −0.18 | 2.50 | 0.31 | 0.58 | 0.64 |
| hsa-miR-145-3p | 0.18 | 3.26 | 0.27 | 0.60 | 0.66 |
| hsa-miR-25-5p | −0.14 | 3.65 | 0.25 | 0.62 | 0.68 |
| hsa-miR-208b-3p | −0.36 | 1.66 | 0.25 | 0.62 | 0.68 |
| hsa-miR-1843 | −0.15 | 2.99 | 0.24 | 0.63 | 0.68 |
| hsa-let-7g-5p | −0.06 | 12.70 | 0.22 | 0.64 | 0.69 |
| hsa-miR-425-5p | −0.06 | 11.21 | 0.22 | 0.64 | 0.69 |
| hsa-miR-550a-3p | −0.17 | 3.72 | 0.20 | 0.66 | 0.71 |
| hsa-miR-651-5p | −0.10 | 4.21 | 0.18 | 0.67 | 0.72 |
| hsa-miR-6803-3p | 0.13 | 2.86 | 0.16 | 0.69 | 0.74 |
| hsa-miR-624-5p | −0.11 | 2.77 | 0.15 | 0.70 | 0.75 |
| hsa-miR-502-3p | 0.07 | 5.01 | 0.14 | 0.71 | 0.76 |
| hsa-miR-1292-5p | 0.09 | 2.72 | 0.12 | 0.73 | 0.77 |
| hsa-miR-141-3p | −0.15 | 6.01 | 0.12 | 0.73 | 0.78 |
| hsa-miR-200b-3p | 0.12 | 4.50 | 0.12 | 0.73 | 0.78 |
| hsa-miR-20b-5p | −0.07 | 7.92 | 0.11 | 0.74 | 0.78 |
| hsa-miR-548at-5p | 0.17 | 2.37 | 0.10 | 0.76 | 0.80 |
| hsa-miR-150-5p | −0.11 | 10.99 | 0.10 | 0.76 | 0.80 |
| hsa-miR-184 | −0.43 | 4.76 | 0.09 | 0.77 | 0.80 |
| hsa-miR-22-3p | 0.04 | 10.13 | 0.08 | 0.77 | 0.81 |
| hsa-miR-215-5p | −0.13 | 5.83 | 0.07 | 0.79 | 0.82 |
| hsa-miR-6734-5p | −0.08 | 2.98 | 0.07 | 0.79 | 0.83 |
| hsa-miR-429 | 0.12 | 3.06 | 0.07 | 0.80 | 0.83 |
| hsa-miR-942-5p | 0.03 | 7.04 | 0.05 | 0.82 | 0.85 |
| hsa-miR-29b-3p | −0.05 | 8.39 | 0.04 | 0.84 | 0.86 |
| hsa-miR-423-5p | −0.06 | 13.29 | 0.04 | 0.84 | 0.86 |
| hsa-miR-1976 | 0.03 | 4.00 | 0.03 | 0.86 | 0.88 |
| hsa-miR-196a-5p | 0.08 | 3.31 | 0.03 | 0.86 | 0.88 |
| hsa-miR-200a-3p | 0.06 | 4.89 | 0.03 | 0.87 | 0.89 |
| hsa-miR-576-3p | −0.04 | 2.64 | 0.02 | 0.89 | 0.91 |
| hsa-miR-18a-3p | 0.03 | 5.26 | 0.01 | 0.91 | 0.92 |
| hsa-miR-532-5p | 0.02 | 7.21 | 0.01 | 0.92 | 0.94 |
| hsa-miR-642a-3p | 0.04 | 1.85 | 0.01 | 0.94 | 0.95 |
| hsa-miR-501-3p | −0.01 | 6.29 | 0.00 | 0.95 | 0.96 |
| hsa-miR-5010-5p | 0.06 | 2.94 | 0.06 | 0.97 | 0.98 |
| hsa-miR-378a-5p | 0.31 | 3.00 | 1.37 | 0.98 | 0.99 |
| hsa-miR-424-5p | 0.01 | 5.90 | 0.00 | 0.98 | 0.99 |
| hsa-miR-106a-5p | 0.00 | 2.84 | 0.00 | 0.99 | 1.00 |
| hsa-miR-5010-3p | 0.07 | 2.96 | 0.08 | 1.00 | 1.00 |

TABLE 2B (Early N = 97)

| miRNA (n = 97) | logFC | logCPM | F | PValue | FDR | Proportion |
|---|---|---|---|---|---|---|
| hsa-miR-335-3p | 3.28 | 5.60 | 67.54 | 0.00 | 0.00 | 1.00 |
| hsa-miR-199a-5p | 3.17 | 6.67 | 60.76 | 0.00 | 0.00 | 0.98 |
| hsa-miR-671-3p | 3.50 | 4.43 | 69.02 | 0.00 | 0.00 | 0.98 |
| hsa-miR-1260b | 3.62 | 4.25 | 65.49 | 0.00 | 0.00 | 0.95 |
| hsa-miR-191-3p | 2.41 | 3.77 | 33.30 | 0.00 | 0.00 | 0.95 |
| hsa-miR-335-5p | 1.91 | 9.31 | 31.92 | 0.00 | 0.00 | 0.95 |
| hsa-miR-543 | 3.59 | 2.90 | 51.76 | 0.00 | 0.00 | 0.95 |
| hsa-miR-1260a | 2.07 | 3.55 | 34.99 | 0.00 | 0.00 | 0.93 |
| hsa-miR-1273h-3p | 3.48 | 3.36 | 57.88 | 0.00 | 0.00 | 0.93 |
| hsa-miR-127-3p | 4.70 | 5.86 | 64.19 | 0.00 | 0.00 | 0.93 |
| hsa-miR-134-5p | 3.61 | 7.61 | 41.22 | 0.00 | 0.00 | 0.93 |
| hsa-miR-146a-5p | 2.53 | 13.34 | 47.86 | 0.00 | 0.00 | 0.93 |
| hsa-miR-28-3p | 2.66 | 8.31 | 56.02 | 0.00 | 0.00 | 0.93 |
| hsa-miR-328-3p | 2.17 | 7.97 | 42.27 | 0.00 | 0.00 | 0.93 |
| hsa-miR-3679-5p | 2.26 | 4.17 | 20.60 | 0.00 | 0.00 | 0.93 |
| hsa-miR-369-3p | 3.69 | 6.45 | 42.97 | 0.00 | 0.00 | 0.93 |
| hsa-miR-376c-3p | 4.30 | 5.08 | 61.52 | 0.00 | 0.00 | 0.93 |
| hsa-miR-381-3p | 4.36 | 6.06 | 58.84 | 0.00 | 0.00 | 0.93 |
| hsa-miR-382-3p | 3.80 | 3.84 | 47.85 | 0.00 | 0.00 | 0.93 |
| hsa-miR-4433b-5p | 4.28 | 6.14 | 78.79 | 0.00 | 0.00 | 0.93 |
| hsa-miR-485-3p | 4.22 | 6.62 | 60.27 | 0.00 | 0.00 | 0.93 |
| hsa-miR-494-3p | 3.77 | 4.76 | 56.83 | 0.00 | 0.00 | 0.93 |
| hsa-miR-584-5p | 1.92 | 9.61 | 31.90 | 0.00 | 0.00 | 0.93 |
| hsa-miR-744-5p | 3.27 | 8.97 | 67.14 | 0.00 | 0.00 | 0.93 |
| hsa-miR-766-3p | 4.44 | 4.44 | 54.00 | 0.00 | 0.00 | 0.93 |
| hsa-let-7e-5p | 2.49 | 9.08 | 55.76 | 0.00 | 0.00 | 0.90 |
| hsa-miR-107 | 4.35 | 4.97 | 84.68 | 0.00 | 0.00 | 0.90 |

TABLE 2B-continued (Early N = 97)

| miRNA (n = 97) | logFC | logCPM | F | PValue | FDR | Proportion |
|---|---|---|---|---|---|---|
| hsa-miR-136-5p | 4.14 | 3.73 | 62.84 | 0.00 | 0.00 | 0.90 |
| hsa-miR-139-3p | 1.85 | 6.11 | 21.64 | 0.00 | 0.00 | 0.90 |
| hsa-miR-151a-3p | 2.46 | 10.69 | 53.98 | 0.00 | 0.00 | 0.90 |
| hsa-miR-181d-5p | 2.60 | 4.40 | 43.71 | 0.00 | 0.00 | 0.90 |
| hsa-miR-223-3p | 2.09 | 14.35 | 52.42 | 0.00 | 0.00 | 0.90 |
| hsa-miR-223-5p | 1.77 | 8.16 | 36.96 | 0.00 | 0.00 | 0.90 |
| hsa-miR-224-5p | 2.84 | 7.75 | 31.38 | 0.00 | 0.00 | 0.90 |
| hsa-miR-2355-3p | 2.43 | 3.35 | 26.76 | 0.00 | 0.00 | 0.90 |
| hsa-miR-3120-3p | 4.06 | 2.02 | 55.50 | 0.00 | 0.00 | 0.90 |
| hsa-miR-329-3p | 4.16 | 3.06 | 48.41 | 0.00 | 0.00 | 0.90 |
| hsa-miR-379-5p | 4.34 | 6.85 | 70.85 | 0.00 | 0.00 | 0.90 |
| hsa-miR-382-5p | 3.18 | 9.00 | 36.53 | 0.00 | 0.00 | 0.90 |
| hsa-miR-409-3p | 4.09 | 8.81 | 56.26 | 0.00 | 0.00 | 0.90 |
| hsa-miR-431-5p | 4.76 | 7.47 | 70.01 | 0.00 | 0.00 | 0.90 |
| hsa-miR-432-5p | 4.39 | 8.92 | 62.12 | 0.00 | 0.00 | 0.90 |
| hsa-miR-4433b-3p | 4.29 | 2.90 | 38.12 | 0.00 | 0.00 | 0.90 |
| hsa-miR-487b-3p | 4.65 | 5.09 | 62.34 | 0.00 | 0.00 | 0.90 |
| hsa-miR-496 | 4.57 | 1.88 | 68.51 | 0.00 | 0.00 | 0.90 |
| hsa-miR-5187-5p | 2.54 | 3.06 | 23.46 | 0.00 | 0.00 | 0.90 |
| hsa-miR-539-3p | 4.46 | 2.51 | 47.65 | 0.00 | 0.00 | 0.90 |
| hsa-miR-548j-5p | 3.42 | 5.16 | 65.07 | 0.00 | 0.00 | 0.90 |
| hsa-miR-556-3p | 3.47 | 2.90 | 50.19 | 0.00 | 0.00 | 0.90 |
| hsa-miR-625-3p | 2.11 | 8.35 | 39.60 | 0.00 | 0.00 | 0.90 |
| hsa-miR-654-3p | 4.38 | 6.75 | 70.24 | 0.00 | 0.00 | 0.90 |
| hsa-miR-760 | 2.45 | 4.40 | 19.84 | 0.00 | 0.00 | 0.90 |
| hsa-miR-889-3p | 4.52 | 4.12 | 60.30 | 0.00 | 0.00 | 0.90 |
| hsa-miR-99b-5p | 2.12 | 8.15 | 45.53 | 0.00 | 0.00 | 0.90 |
| hsa-miR-1277-5p | 2.13 | 5.72 | 36.26 | 0.00 | 0.00 | 0.88 |
| hsa-miR-1301-3p | 2.40 | 3.79 | 41.60 | 0.00 | 0.00 | 0.88 |
| hsa-miR-139-5p | 1.03 | 5.01 | 11.87 | 0.00 | 0.00 | 0.88 |
| hsa-miR-181c-3p | 3.20 | 3.60 | 54.33 | 0.00 | 0.00 | 0.88 |
| hsa-miR-23b-3p | 1.79 | 10.21 | 50.70 | 0.00 | 0.00 | 0.88 |
| hsa-miR-26a-1-3p | 3.67 | 3.69 | 58.70 | 0.00 | 0.00 | 0.88 |
| hsa-miR-299-5p | 4.07 | 2.11 | 43.13 | 0.00 | 0.00 | 0.88 |
| hsa-miR-3184-5p | 1.93 | 8.05 | 45.17 | 0.00 | 0.00 | 0.88 |
| hsa-miR-323a-3p | 3.44 | 4.65 | 49.35 | 0.00 | 0.00 | 0.88 |
| hsa-miR-339-5p | 2.62 | 7.33 | 50.25 | 0.00 | 0.00 | 0.88 |
| hsa-miR-33a-5p | 1.98 | 3.11 | 22.18 | 0.00 | 0.00 | 0.88 |
| hsa-miR-340-5p | 2.01 | 8.25 | 41.24 | 0.00 | 0.00 | 0.88 |
| hsa-miR-369-5p | 3.78 | 5.64 | 53.75 | 0.00 | 0.00 | 0.88 |
| hsa-miR-377-3p | 3.12 | 3.40 | 40.96 | 0.00 | 0.00 | 0.88 |
| hsa-miR-411-5p | 4.79 | 4.84 | 69.45 | 0.00 | 0.00 | 0.88 |
| hsa-miR-423-3p | 1.84 | 9.76 | 43.27 | 0.00 | 0.00 | 0.88 |
| hsa-miR-425-3p | 2.20 | 5.28 | 36.82 | 0.00 | 0.00 | 0.88 |
| hsa-miR-4446-3p | 4.05 | 3.29 | 44.20 | 0.00 | 0.00 | 0.88 |
| hsa-miR-485-5p | 3.29 | 4.54 | 44.24 | 0.00 | 0.00 | 0.88 |
| hsa-miR-491-5p | 2.46 | 4.05 | 43.45 | 0.00 | 0.00 | 0.88 |
| hsa-miR-493-3p | 4.44 | 4.40 | 48.14 | 0.00 | 0.00 | 0.88 |
| hsa-miR-493-5p | 4.30 | 5.35 | 58.28 | 0.00 | 0.00 | 0.88 |
| hsa-miR-5189-5p | 2.84 | 1.79 | 30.57 | 0.00 | 0.00 | 0.88 |
| hsa-miR-548a-3p | 3.36 | 2.71 | 46.11 | 0.00 | 0.00 | 0.88 |
| hsa-miR-628-5p | 2.50 | 5.01 | 44.39 | 0.00 | 0.00 | 0.88 |
| hsa-miR-671-5p | 1.56 | 4.97 | 16.09 | 0.00 | 0.00 | 0.88 |
| hsa-miR-6852-5p | 4.05 | 2.84 | 45.19 | 0.00 | 0.00 | 0.88 |
| hsa-miR-126-3p | 1.76 | 14.49 | 45.62 | 0.00 | 0.00 | 0.85 |
| hsa-miR-127-5p | 4.58 | 1.73 | 57.59 | 0.00 | 0.00 | 0.85 |
| hsa-miR-146b-5p | 1.89 | 8.68 | 40.87 | 0.00 | 0.00 | 0.85 |
| hsa-miR-152-3p | 1.00 | 6.92 | 11.75 | 0.00 | 0.00 | 0.85 |
| hsa-miR-155-5p | 0.99 | 8.96 | 18.08 | 0.00 | 0.00 | 0.85 |
| hsa-miR-27b-3p | 0.87 | 10.14 | 11.71 | 0.00 | 0.00 | 0.85 |
| hsa-miR-30e-3p | 1.77 | 7.42 | 52.27 | 0.00 | 0.00 | 0.85 |
| hsa-miR-323b-3p | 3.66 | 5.59 | 41.74 | 0.00 | 0.00 | 0.85 |
| hsa-miR-337-5p | 3.46 | 4.39 | 47.98 | 0.00 | 0.00 | 0.85 |
| hsa-miR-370-3p | 4.83 | 5.26 | 57.44 | 0.00 | 0.00 | 0.85 |
| hsa-miR-376a-3p | 4.42 | 3.42 | 56.84 | 0.00 | 0.00 | 0.85 |
| hsa-miR-4662a-5p | 1.50 | 2.59 | 13.61 | 0.00 | 0.00 | 0.85 |
| hsa-miR-625-5p | 2.49 | 5.36 | 42.66 | 0.00 | 0.00 | 0.85 |
| hsa-miR-664b-5p | 1.83 | 2.77 | 18.13 | 0.00 | 0.00 | 0.85 |
| hsa-miR-6842-3p | 1.94 | 2.96 | 22.54 | 0.00 | 0.00 | 0.85 |
| hsa-miR-9-5p | 1.92 | 2.68 | 34.03 | 0.00 | 0.00 | 0.85 |

TABLE 20

(Late N = 3)

| miRNA (n = 3) | logFC | logCPM | F | PValue | FDR | Proportion |
|---|---|---|---|---|---|---|
| hsa-miR-193b-5p | −1.34 | 3.59 | 11.50 | 0.00 | 0.00 | 0.62 |
| hsa-miR-193a-5p | −1.01 | 6.52 | 10.39 | 0.00 | 0.00 | 0.52 |
| hsa-miR-455-5p | −2.74 | 1.44 | 24.35 | 0.00 | 0.00 | 0.50 |

Discussion

Using an optimized protocol for sequencing microRNAs, we identified a distinct panel of 11 circulating microRNAs in early symptomatic knee OA, which included 4 novel microRNAs. We used biologically meaningful prioritization methods to identify 215 microRNAs that were differentially expressed between early and late OA cohorts, 97 of which were consistently higher in ≥85% of early OA samples as compared to late OA samples. Further filtering revealed 7 microRNAs that were able to separate early OA and late OA samples based on their presence in a ≥95% of early OA samples. The sensitivity and specificity of sequencing technology provided the capacity to discover novel microRNAs based on their predicted secondary structure and lack of homology with murine microRNAs. We found 13 novel microRNAs that were present in ≥50% of samples within a group, 9 of which had not been previously described (21). Since there remain uncharacterized tissue-specific microRNAs (21), the 9 novel microRNAs identified here could be OA-specific, and the 4 novel microRNAs identified in the early OA cohort merit further investigation as OA-stage-specific markers.

Discovery of this panel of 11 microRNAs was facilitated by careful selection of our early and late symptomatic radiographic knee OA cohorts. While defining early stages of knee OA has proved challenging, three categorical criteria were proposed by Luyten and colleagues (2018), including (a) pain, symptoms/signs, self-reported function, and quality of life; (b) clinical examination with at least 1 of joint line tenderness or crepitus; and (c) knee radiographs showing Kellgren-Lawrence (KL) grade 0 or 1 (31). All patients in our early OA group met these criteria as well as American College of Rheumatology clinical criteria for knee OA classification (17). While patients with any type of arthritis other than OA were excluded, some patients may have had multiple joints affected by OA, with varying stages of severity. Other limitations of our study include the lack of healthy samples with which to compare microRNA panels, and the imbalance of race and age between groups. Although statistical measures were used to correct for race and age, validation in independent cohorts that include healthy samples is required to determine the utility of the microRNAs identified here as potential biomarkers for early knee OA.

Given the stability and ease of detection of plasma microRNAs (4, 5), they represent good candidates for biomarkers of OA. Biochemical and imaging techniques have previously been applied to OA biomarker discovery, but there is still a lack of highly specific and sensitive biomarkers that can be used for OA diagnosis, prognosis, or staging (32, 33). Unlike studies that use arrays or sequencing to identify candidates of interest in only a subset of their cohort, a major strength of our study was the use of sequencing to profile the entire cohort of 91 samples. As described by Kok et al., small sample sizes (<25 per group) in high-throughput microRNA screens are a common pitfall for the identification of biomarkers given the limited reproducibility (19). Our first filtering step was to select microRNAs with high abundance (≥10 CPM in ≥2 samples), to increase the likelihood of detection in independent cohorts. We then normalized the results by total counts rather than using traditional methods such as trimmed mean of m-values, which can mask differences between groups by assuming that the majority of microRNAs are not differentially expressed (34). These methodological decisions led us to discover a panel of 11 microRNAs with increased likelihood for reproducibility.

The circulating microRNAs we identified may reflect an early signal that induces a cascade of events that contribute to OA. Experimental validation of our findings is required to identify the source and target tissue(s) of the microRNAs, whether it be the cartilage, synovium, bone, adipose tissue, or others. Among the top 11 microRNAs identified, hsa-miR-335-3p and -5p were highly expressed in 100% and 95% of early OA samples, respectively. Arms of miR-335 are expressed in osteoblasts (36) and mesenchymal stem cells (37), with a role in promoting chondrogenesis (38). The presence of these microRNAs in the blood plasma suggests that they may act systemically to impact more than one joint or target tissue. Animal models, where it is possible to modulate microRNAs genetically or pharmacologically, are required to investigate the potential impact of these microRNAs in OA pathophysiology. Elucidating the biological mechanism of these microRNAs may have therapeutic relevance since microRNAs can be targeted with antisense oligonucleotides (39). Given our clinically relevant cohort of patients with early radiographic features of OA, and the optimized microRNA sequencing methodology that was applied, our results reflect a distinct panel of circulating microRNAs in early knee OA.

Example 2

Methods
Early and Late Symptomatic Radiographic Knee OA Cohorts

In this study, we utilized blood plasma samples from three knee OA cohorts, including two early OA cohorts (early radiographic knee OA defined by Kellgren-Lawrence grade 0 or 1) and one late OA cohort (late radiographic knee OA defined by Kellgren-Lawrence grade 3 or 4). All patients were symptomatic and fulfilled the American College of Rheumatology clinical criteria for knee OA classification (17). With informed consent, demographic, anthropometric, and clinical data were collected for each patient. Blood samples were collected in K2-EDTA tubes and centrifuged at 4000 rpm for 10 minutes at 4° C. The resulting plasma supernatant was aliquotted into 250 uL per cryovial, flash frozen with liquid nitrogen, and stored in a cryo freezer until use. Only plasma samples that were never previously thawed were used in this study.

Our first cohort, The Arthritis Program Early Knee OA cohort, at the University Health Network (UHN; Toronto, Canada), comprised plasma samples (n=22) obtained from patients scheduled to undergo knee arthroscopy with Kellgren-Lawrence grade 1 and experiencing persistent pain for at least 4 weeks. These patients were diagnosed by orthopaedic surgeon R.G. Our second cohort, the Western Ontario Registry for Early Osteoarthritis (WOREO) Knee Study, at the University of Western Ontario (London, Canada), included plasma samples (n=19) from patients referred to the St. Joseph's Health Care London Rheumatology Centre with symptomatic early OA (Kellgren-Lawrence grade 0 or 1) who answered 'yes' to having frequent knee symptoms on most days for at least 4 weeks, with no alternative explanation for knee pain including other rheumatic diseases or acute injuries. These patients were diagnosed by rheumatologist T.A. Our third cohort, the late OA cohort, included plasma samples (n=50) from our Longitudinal Evaluation in the Arthritis Program (LEAP) cohort (UHN; Toronto, Canada) comprised of patients scheduled to undergo total knee arthroplasty surgery exhibiting Kellgren-Lawrence grades 3 and 4 (study design is described in FIG. 1).

Sequencing of microRNAs

A total of 99 plasma samples were subjected to library preparation for sequencing of microRNAs. RNA was extracted from 200 μL of human plasma using the QIAcube semi-automated system following manufacturer's instructions for sample setup of the miRNeasy Serum/Plasma Advanced Kit (Qiagen, Hilden, Germany). RNA eluate (18 μL in nuclease-free water) was stored at −80° C. cDNA libraries (n=50 for late OA; n=49 for early OA) were prepared from 5 μL RNA using the QIAseq miRNA Library Kit according to manufacturer's recommendations for biofluid samples, including 3' and 5' adapter and RT primer dilutions and a 22-cycle library amplification. A detailed protocol is provided in Example 3. A key advantage of this method is that unique molecular indexes (UMIs) are incorporated during cDNA synthesis, uniquely tagging each strand prior to amplification, which more accurately reflects endogenous microRNA levels by controlling for library amplification bias.

Individual libraries were quantified using a fluorometric high sensitivity dsDNA assay (DeNovix, Wilmington, DE, USA). Library quality was assessed on a high sensitivity DNA chip on the Bioanalyzer (Agilent, Santa Clara, CA, USA). Sample libraries were divided into batches across 5 sequencing runs where sample groups were distributed. On the day of sequencing, library batches were pooled, re-quantified (DeNovix), denatured and diluted to 1.5 pM, and spiked with 1% PhiX Sequencing Control V3 library, which acts as a quality metric for cluster generation, sequencing, and alignment. Spiked library pools were sequenced on Illumina's NextSeq550 system using a high-output kit v2 following a 76-base single read protocol (Illumina, San Diego, CA, USA) at the Arthritis Centre for Diagnostic and Therapeutic Innovation (Krembil Research Institute, Toronto, ON, Canada).

Sequencing Data Alignment and Counts Generation

An overview of this method is provided in FIG. 5. Demultiplexing of .bcl files and conversion into Fastq files was performed, followed by flagging quality parameters such as insufficient number of reads (<400 000 reads), low sequence quality scores (<Q20), low percentage duplication (20%), and poor 3' adapter contamination (<40%) in reads. Random UMIs of 12 bp length were extracted from the sequence part of the read and placed in the header part of the same read in the Fastq file. This is a crucial step for later deduplication of reads to reduce PCR amplification bias. Regular expression pattern was used in UMI-tools software to select reads containing less than 2 mismatches in the 3' adapter sequence mentioned, followed by a 12 bp random UMI tag sequence, and the remaining part of the read was discarded. We discarded reads of less than 18 bp as too short and reads greater than 30 bp as too long given that microRNAs are typically 22-25 bp in length.

Alignment of reads was carried out against mature microRNA sequences from miRBase v22.1 with the following parameters: no mismatches in a seed read length of 30 bp, no alignment to forward/reverse-complement reference strand, and reporting only the best hits found in a strata of reads. Unaligned reads were kept separate from this step. Deduplication of aligned reads based on UMIs was performed to correctly assign the number of reads for each mature microRNA in miRBase v22.1, providing read counts. The second round of alignment involved using the unaligned reads against the human reference genome (vGRCh38) with the same parameters except allowing one mismatch instead of zero. Annotation was performed only for those regions in the aligned file which fell between the chromosomal coordinates of human mature microRNAs from miRBase v22.1. Counts were generated based on reads mapping onto the genome coordinates. Finally, each microRNA from miRBase v22.1 was assigned a combined total count of mature microRNA reads as well as genome based mature microRNA region reads mapping to 2656 mature microRNAs.

Statistics

Samples with low numbers of aligned reads were removed from the analysis based on quality parameters described above and based on having log-reads below the 0.025 normal quantile of the log-reads distribution across all samples. A total of 8 early OA samples were removed based on these criteria, resulting in 91 samples for analysis. MicroRNAs were filtered to have at least 10 counts-per-million (CPM) of classified sequences in at least 2 samples. For principal component analysis, counts were transformed using variance stabilizing transformation in order to stabilize the variance across the mean before plotting (40). Inference was performed on the raw counts using a negative binomial regression estimated by quasi-likelihood (41) with trended dispersion and normalized by total aligned sequences. The trimmed mean of m-values (TMM) method was not applied as a large number of the microRNAs were differentially expressed between the early OA group versus the late OA group, violating the TMM assumptions (34). Covariates potentially affecting differential expression between microRNAs were screened using univariate models. A final list of differentially expressed microRNAs between early OA and late OA samples was obtained using a multivariate model adjusted for age, sex, BMI, race, collection site, and batch, and filtered using a false discovery rate (FDR) of 0.01, estimated by the Benjamini-Hochberg (BH) method. The analysis was implemented in R 3.6.1 using the edgeR package (v3.28.0). This list was filtered for biological relevance by including microRNAs in which the expression levels for at least 85% of the samples in the early OA group exceeded the median expression of the late OA group, and microRNAs in which the expression levels for at least 50% of the samples in the late OA group exceeded the median expression of the early OA group.

Novel microRNA Analysis

Discovery of novel microRNAs was performed using miRDeep v2 (42). This did not include processing of UMI tags, instead duplicate reads were removed based on the read alone. Hence, we extracted the UMI tag from the reads so that it did not interfere with the actual microRNA portion of the reads during the alignment to the human reference genome (vGRCh38). The aligned files were then used by miRDeep2.pl script, where novel mature and hairpin microRNA sequences were discovered by providing human mature and hairpin microRNA sequences along with mouse mature microRNA sequences for homology assessment. Using custom scripts, only those mature microRNAs were selected which had a significant randfold score and no homology with mouse mature microRNAs. We then selected those microRNAs which were expressed in at least 50% of samples in each group.

Example 3

MicroRNA-Sequencing Library Preparation (for 12 Samples)

Day 1: MicroRNA Isolation from Human Plasma

Protocol using QIAcube and Qiagen miRNeasy Serum/Plasma Advanced Kit (Cat #217204) available upon request End product: 18 uL eluate of small RNAs in nuclease free water, aliquotted into 2 tubes of 10 uL (for backup storage) and 8 uL (for use on Day 2)

Day 2: MicroRNA Library Preparation

Protocol using Qiagen QIAseq miRNA Library Kit [Cat #331505 (96 reactions)] and QIAseq miRNA NGS 96 Index IL [Cat #331565 (breakable 96-well plate)]

Materials

Box 1 of library kit stored at −20° C.
Box 2 of library kit stored at 4° C.
Index kit stored at −20° C.
Plate magnet for 8-well strips
Tube magnet for 2 mL tubes
Thermocycler for 8-well strips with reaction volume of up to 60 uL
Desktop tube centrifuge and strip centrifuge, and flat-top vortexer
Nuclease free water
80% ethanol with nuclease free water (55 mL prepared on Day 1)
    44 mL RNA-only ethanol
    11 mL nuclease free water
6×1.5 mL eppendorf tubes to prepare primer dilutions and mastermixes
6 strip tubes of 8 wells with 0.2 mL volume, several strip cap covers
    IMPORTANT: LABEL all strips with number at one end to maintain orientation
Plastic plate seal covers for 96-well plate cut into 6 strips
96-well plate cooling block to place in ice bucket Methods 4 parts: A) 3' Ligation, B) 5' Ligation, C) Reverse Transcription, D) cDNA cleanup
    IMPORTANT: Prepare 3' and 5' ligation reactions and reverse transcription on ice
    IMPORTANT: Reaction components should be added in the order listed
    IMPORTANT: Do not vortex template RNA, NGS RI, NGS 3' ligase, 3' ligation reactions (Part A), NGS 5' ligase, 5' ligation reactions (Part B), NGS RT enzyme, reverse transcription reactions (Part C)
    IMPORTANT: Use same desktop centrifuge for all 'Spin' steps (press & hold 5 s)

Part A: 3' ligation using 5 uL from 8 uL miRNA aliquot stored at −20° C. from Day 1

1. Thaw 8 uL aliquot of 12 samples of template microRNA on ice
2. Thaw 3 kit reagents at room temperature: NGS 3' adapter, 3' buffer, ligation activator
3. During thaw, mix each microRNA sample:
    a. Spin 5 seconds
    b. Mix by pipetting 5 uL up and down 10 times
    c. Spin 5 seconds, place on ice
4. Mix each of 3 kit reagents by flicking tubes 10 times each (turn tubes upside down)

a. Ensure ligation activator is completely dissolved at room temp and there is no white precipitate (will dissolve with mixing)
5. Quick spin 3 kit reagents for 5 seconds, keep at room temperature
6. Dilute NGS 3' adapter at room temperature (1:5 dilution, 1 uL per sample required)
   a. For 12 samples=4 uL adapter+16 uL nuclease free water
   b. Spin 5 seconds
   c. Mix by pipetting 16 uL up and down 12 times
   d. Spin 5 seconds
7. Place 2 kit reagents on ice: NGS RI, 3' RNA Ligase
   a. Flick both 10 times (turn tube upside down) and quick spin 5 seconds
      i. IMPORTANT: Return to −20° C. immediately after use
8. Prepare 3' mastermix on ice, for 12 samples and 10% extra, multiply by 13.2; mix each reagent tube 5-10 times before pipetting final volume:
   a. NGS 3' adapter (1 uL, diluted at room temp in step 6)=13.2 uL
   b. NGS RI (1 uL, enzyme on ice)=13.2 uL
   c. 3' ligase (1 uL, enzyme on ice)=13.2 uL
   d. 3' buffer (2 uL, at room temp)=26.4 uL
   e. Ligation activator (10 uL, at room temp, viscous)=132 uL
      i. IMPORTANT: ensure there are no extra droplets outside the pipette tip before adding & no remaining droplets inside the pipette tip after adding
9. Mix 3' mastermix
   a. Spin 5 seconds
   b. Mix by pipetting 150 uL up and down 20 times, stir with pipette tip every 5th time
      i. IMPORTANT: mix slowly, below surface of liquid, very viscous
   c. Spin 5 seconds
10. Total volume of 3' mastermix=198 uL □ add 15 uL directly to each of 12 empty wells in 2 strips of wells on ice—use plate cooling block
    i. IMPORTANT: pay attention for extra/residual droplets on pipette tip, ensure precise volume is pipetted in each well
    ii. IMPORTANT: LABEL all strips at one end to maintain orientation
11. Add 5 uL microRNA sample to each well with 3' mastermix
    a. Cover temporarily with strip caps but do not secure, spin 5 seconds
    b. Remove strip cap cover, mix each well by pipetting 15 uL 20 times
       i. IMPORTANT: Approximately 30 min to mix 12 samples, ensure no droplets left in tip, mix slowly and below the surface of the liquid
    c. Cover with same strip caps, secure and spin 5 seconds
12. Put the 2 strips into a thermocycler (20 uL volume)
    a. 28° C. for 1 hour
    b. 65° C. for 20 min
    c. 4° C. hold for at least 5 min
       BREAK: 1 HOUR 25 MIN
       After 30 min thaw 5' adapter and 5' buffer at room temperature After 1 hour begin preparing 5' mastermix Part B: 5' ligation using entire 20 ul from above (strips placed on ice in cooling block)

13. Thaw 2 kit reagents at room temperature: NGS 5' adapter, 5' buffer
    a. Mix by flicking tube 10 times (turn upside down)
    b. Spin 5 seconds
14. Dilute NGS 5' adapter at room temperature (1:2.5 dilution, 1 uL per sample required)
    a. For 12 samples=8 uL adapter+12 uL nuclease free water
    b. Spin 5 seconds
    c. Mix by pipetting 12 uL up and down 12 times
    d. Spin 5 seconds
15. Place 2 kit reagents on ice: NGS RI, 5' RNA Ligase
    a. Flick ligase 10 times (turn tube upside down) and quick spin 5 seconds
       i. IMPORTANT: Return to −20° C. immediately after use
16. Prepare 5' mastermix on ice, for 12 samples and 10% extra, multiply by 13.2:
    a. Nuclease free water (15 uL, at room temp)=198 uL
    b. 5' buffer (2 uL, at room temp)=26.4 uL
    c. NGS RI (1 uL, enzyme on ice)=13.2 uL
    d. 5' ligase (1 uL, enzyme on ice)=13.2 uL
    e. NGS 5' adapter (1 uL, diluted at room temp in step 14)=13.2 uL
17. Mix 5' mastermix
    a. Spin 5 seconds
    b. Mix by pipetting 200 uL up and down 20 times
       i. IMPORTANT: mix slowly, below surface of liquid
    c. Spin 5 seconds
18. Remove strips from thermocycler and spin 5 seconds
19. Total volume of 5' mastermix=264 uL □ gently remove caps (avoid splashing/creating droplets), add 20 uL mastermix directly to each of 12 wells on ice:
    a. Cover temporarily with same strip caps but do not secure, spin 5 seconds
    b. Remove cover, mix by pipetting 35 uL up and down 20 times
    c. Cover securely with new strip caps and spin 5 seconds
20. Put the 2 strips into a thermocycler (40 uL volume)
    a. 28° C. for 30 min
    b. 65° C. for 20 min
    c. 4° C. hold
       [BREAK: 50 MIN]
       After 30 min thaw NGS RT initiator, RT buffer, RT primer Part C: Reverse Transcription using entire 40 ul from above (strips placed on ice)

21. Thaw 3 kit reagents at room temperature: NGS RT initiator, RT buffer, RT primer
    a. Mix by flicking tube 10 times
    b. Spin
22. Remove strips from thermocycler and spin 5 seconds
23. Add 2 uL RT initiator to each well
    a. Cover loosely with same strip caps and spin 5 seconds
    b. Remove cover, mix by pipetting 35 uL up and down 20 times
    c. Cover securely with new strip caps and spin 5 seconds
24. Put the 2 strips into a thermocycler (42 uL volume)
    a. 75° C. for 2 min
    b. 70° C. for 2 min
    c. 65° C. for 2 min
    d. 60° C. for 2 min
    e. 55° C. for 2 min
    f. 37° C. for 5 min g. 25° C. for 5 min
h. 4° C. hold
25. While in thermocycler (~20 min), continue with next steps (reagents already thawed)
26. Dilute RT primer at room temperature (1:5 uL dilution, 2 uL per sample required)
   a. For 12 samples=8 uL primer+32 uL nuclease free water
   b. Spin 5 seconds
   c. Mix by pipetting 32 uL up and down 12 times
   d. Spin 5 seconds
27. Place 2 kit reagents on ice: NGS RI, RT enzyme
   a. Flick enzyme 10 times (turn tube upside down) and quick spin 5 seconds
      i. IMPORTANT: Return to −20° C. immediately after use
28. Prepare RT mastermix on ice, for 12 samples and 10% extra, multiply by 13.2:
   a. RT primer (2 uL, diluted at room temp in step 26)=26.4 uL
   b. Nuclease free water (2 uL, at room temp)=26.4 uL
   c. RT buffer (12 uL, at room temp)=158.4 uL
   d. NGS RI (1 uL, enzyme on ice)=13.2 uL
   e. RT enzyme (1 uL, enzyme on ice)=13.2 uL
29. Mix RT mastermix
   a. Spin 5 seconds
   b. Mix by pipetting 200 uL up and down 20 times
      i. IMPORTANT: mix slowly, below surface of liquid
   c. Spin 5 seconds
30. Remove strips from thermocycler and spin 5 seconds
31. Total volume of RT mastermix=237.6 uL □ add 18 uL directly to each of 12 wells on ice:
   a. Cover loosely with same strip caps and spin 5 seconds
   b. Remove cover, mix by pipetting 50 uL up and down 20 times
   c. Cover securely with new strip caps and spin 5 seconds
32. Put the 2 strips into a thermocycler (60 uL volume)
   a. 50° C. for 60 min
   b. 70° C. for 15 min
   c. 4° C. hold for at least 5 min
      [BREAK: 1 HOUR 20 MIN]
      Prepare QMN Beads during the break
      QIAseq miRNA NGS Beads=QMN Beads

[QIAseq beads+QIAseq miRNA NGS Bead Binding Buffer=QMN Beads]

IMPORTANT: Beads stored at 4° C., need to be constantly vortexed and kept on ice
33. Invert 10 times and vortex QIAseq beads for 20 seconds—DO NOT SPIN
34. For 12 samples (245.5 uL QMN beads required per sample), aliquot 1.6 mL QIAseq beads (viscous, pipette carefully) to 2 separate 2 mL conical tube
   a. Total volume of beads required for 12 samples=2.946 mL
   b. Total volume of beads prepared in 2 conical tubes=3.2 mL (~10% extra)
35. Spin 2 conical tubes 5 seconds
36. Place 2 conical tubes on magnet stand for 15 minutes (complete bead migration)
37. Remove and discard supernatant (acceptable to leave residual supernatant)
38. Remove tubes from magnet stand, place at room temp
39. Invert 10 times and vortex QIAseq miRNA NGS Bead Binding buffer for 20 seconds—DO NOT SPIN
40. Pipette 600 uL NGS Bead Binding buffer (viscous, pipette carefully) over the beads in each of the 2 tubes
41. Invert 10 times and vortex for 20 seconds (thoroughly resuspend bead pellet)
42. Spin 2 conical tubes
43. Place 2 conical tubes on magnet stand for 15 minutes (complete bead migration)
44. Remove and discard supernatant (remove as much as possible, do not disturb beads)
45. Remove tubes from magnet stand, place at room temp
46. Pipette 1.6 mL NGS Bead Binding buffer (viscous, pipette carefully) over the beads in each of the 2 tubes
47. Vortex for 20 seconds (resuspend bead pellet)
48. Store on ice until use (store at 4° C. for re-use on Day 3)

Part D: cDNA cleanup
49. Obtain 2 strips from thermocycler, spin 5 seconds at room temp
50. Invert 2 aliquots of QMN beads 10 times, vortex for 20 seconds (resuspend bead pellet)
51. Place strips on ice, remove cover
52. Add 135 uL QMN beads to each of 12 wells containing 60 uL cDNA
53. Cover with plastic seal (wells are full, be careful they do not spill over)
   i. IMPORTANT: DO NOT USE STRIP CAPS, wells will overflow
54. Vortex for 3 seconds (use flat-top vortexer—short vortex in pulses, protect sample)
55. Spin at 2000 rpm for 2 min at room temperature (place strips into 96-well plate, use large centrifuge)
56. Incubate at room temperature for 5 minutes (with plastic seal cover on)
57. Place strips on plate magnet for 20 minutes total (for complete bead migration)
   a. After 10 minutes, remove & discard 50 uL
   b. After 15 minutes, remove & discard another 50 uL
   c. After 20 minutes, remove & discard remaining 100 uL (do not disturb beads)
58. Add 200 uL of 80% ethanol over the beads while still on magnet
59. Quickly move strip to push beads back and forth through ethanol four times
   a. Position 1 to 2 (beads move 1×)
   b. Position 2 to 1 (beads move 2×)
   c. Position 1 to 2 (beads move 3×)
   d. Position 2 to 1 (beads move 4× and are back in original position)
60. Remove and discard ethanol (acceptable to leave residual ethanol)
61. Add 200 uL of 80% ethanol again, over the beads while on magnet
62. Quickly move strip to push beads back and forth through ethanol four times (as described in step 59)
63. Remove and discard ethanol (remove as much as possible, do not disturb beads)
64. Place caps on strips
65. Spin 5 seconds at room temp
66. Remove caps, place strips on magnet
67. Remove any residual ethanol with a 20 uL pipette
68. Leave beads on magnet stand (with cap removed) to air dry for 15 minutes
   a. Visually inspect for cracking to ensure beads are dry (see FIG. 1)
   b. Ensure all residual ethanol in the well has evaporated
69. Add 17 uL of nuclease free water over the beads while still on magnet 70. Remove from magnet
71. Pipette up and down 15 times
72. Place caps on strips
73. Spin at 2000 rpm for 2 min at room temp (place strips into plate, use large centrifuge)
74. Incubate at room temperature for 2 min
75. Return strips to plate magnet for 2 min (complete bead migration)
76. Remove caps, transfer 16 uL of eluted DNA to new strips
    i. IMPORTANT: LABEL all strips at one end to maintain orientation
77. Replace new caps, spin 5 sec Q REPEAT transfer to remove beads
78. Return strips to plate magnet, transfer ~15 uL of eluted DNA to new (final) strips
    i. IMPORTANT: LABEL all strips at one end to maintain orientation
79. Secure caps, spin 5 seconds, store strips at −20° C. overnight Day 3: MicroRNA Library Preparation Continued
Materials
  QMN beads prepared on Day 2
  Same equipment/instruments used on Day 2
  6 strip tubes of 8 wells with 0.2 mL volume, 6 strip cap covers
Methods
  IMPORTANT: Prepare library amplification reaction on ice
  IMPORTANT: LABEL all strips at one end to maintain orientation
  IMPORTANT: Do not vortex DNA polymerase or library amplification reaction
Library Amplification:
1. Thaw 12 samples (2 strips) on ice
2. Thaw 1 kit reagent at room temperature: NGS Library Buffer
    a. Mix by flicking tube 10 times (turn tube upside down)
    b. Spin 5 seconds
       i. If precipitate still remains at bottom of tube, do not disturb
3. Place 1 kit reagent on ice: HotStarTaq DNA Polymerase
    i. IMPORTANT: Return to −20° C. immediately after use
4. Prepare amplification mastermix on ice, for 12 samples and 10% extra, multiply by 13.2:
    a. Library buffer (8 uL, at room temp)=105.6 uL
    b. DNA polymerase (1.5 uL, enzyme on ice)=19.8 uL
    c. Nuclease free water (15.5 uL, at room temp)=204.6 uL
5. Mix amplification mastermix
    a. Spin 5 seconds
    b. Mix by pipetting 204 uL up and down 15 times
    c. Spin 5 seconds
6. Spin 2 strips 5 seconds
7. Place strips with 15 uL DNA on magnet (to remove residual beads during transfer)
8. Open QIAseq miRNA NGS 96 Index IL index plate (stored at −20° C.)
    a. Use scissors to cut 1 full row of 12 wells
    b. E.g. Row A=MIHT1, MIHT9, MIHT17 etc
9. Transfer ~12-13 uL DNA from strips to kit plate, noting the order
    a. Each sample must correspond to a specific index (MIHTx)
10. Total volume of amplification mastermix=330 uL □ add 25 uL directly to each of 12 wells in kit plate on ice in cooling block
    a. Mix by pipetting 25 uL up and down 12 times
    b. Place caps (provided in kit) on strips
    c. Spin 2000 rpm for 2 min at room temp (place strips into plate, use big centrifuge)
11. Put the 2 strips into a thermocycler (40 uL volume)
    a. 95° C. for 15 min
    b. 3-step cycle:
       i. 95° C. for 15 sec
       ii. 60° C. for 30 sec
       iii. 72° C. for 15 sec
       iv. Repeat for 22 cycles
    c. 72° C. for 2 min
    d. 4° C. hold for at least 5 min
    [BREAK: 60 MIN]
12. Spin 2000 rpm for 2 min at room temp (place strips into plate, use big centrifuge)
13. Retrieve QMN beads from Day 2 from fridge, invert 10 times and vortex for 20 seconds
14. Place strips on ice in cooling block, remove cover
15. Add 37.5 uL QMN beads to each of 12 wells containing 40 uL cDNA
16. Cover with plastic seal strip (cut into 6 strips from full plate seal cover)
17. Vortex for 3 seconds (use flat-top vortexer—short vortex in pulses, protect sample)
18. Spin at 2000 rpm for 2 min at room temp (place strips into plate, use big centrifuge)
19. Incubate at room temperature for 5 min
20. Place strips on plate magnet for 5 minutes (for complete bead migration)
21. Transfer supernatant (~75 uL) to NEW STRIPS
    i. IMPORTANT: keep supernatant, discard beads/old strips
    ii. IMPORTANT: LABEL all strips at one end to maintain orientation
22. Repeat transfer of supernatant (~70 uL) to NEW STRIPS to ensure no residual beads
    i. IMPORTANT: LABEL all strips at one end to maintain orientation
23. Remove from magnet
24. Invert QMN beads 10 times and vortex for 20 seconds
25. Add 65 uL QMN beads to each of 12 wells containing ~70 uL supernatant
26. Cover with plastic seal strip (cut into 6 strips from full plate seal cover)
27. Vortex for 3 seconds (use flat-top vortexer–short vortex in pulses, protect sample)
28. Spin at 2000 rpm for 2 min at room temp (place strips into plate, use big centrifuge)
29. Incubate at room temperature for 5 min
30. Place strips on plate magnet for 5 minutes (for complete bead migration)
31. Remove and discard supernatant (~140 uL) without disturbing beads
    i. IMPORTANT: keep the beads, discard supernatant
32. Add 200 uL of 80% ethanol over the beads while still on magnet
33. Quickly move each strip to push beads back and forth through ethanol four times
    a. Position 1 to 2 (beads move 1×)
    b. Position 2 to 1 (beads move 2×)
    c. Position 1 to 2 (beads move 3×)
    d. Position 2 to 1 (beads move 4× and are back in original position)

34. Remove and discard ethanol (acceptable to leave residual ethanol)
35. Add 200 uL of 80% ethanol again, over the beads while on magnet
36. Quickly move each strip to push beads back and forth through ethanol four times as described in step 33
37. Remove and discard ethanol (remove as much as possible, do not disturb beads)
38. Place caps on strips
39. Quick spin 5 seconds
40. Remove caps, place strips on magnet
41. Remove any residual ethanol with a 20 uL pipette
42. Leave beads on magnet stand (with cap removed) to air dry for 15 minutes
    a. Visually inspect for cracking to ensure beads are dry (see FIG. 1 above)
    b. Ensure all residual ethanol in the well has evaporated
43. Add 17 uL of nuclease free water over the beads while still on magnet
44. Remove from magnet
45. Pipette up and down 15 times
46. Place caps on strips
47. Spin at 2000 rpm for 2 min at room temp (place strips into plate, use big centrifuge)
48. Incubate at room temperature for 2 min
49. Return strips to plate magnet for 2 min (complete bead migration)
50. Remove caps, transfer 15 uL of eluted DNA to new strips or tubes in 5 uL aliquots:
    a. FIRST 5 uL=for storage (−80° C., backup sample)
    b. SECOND 5 uL=for sequencing (−20° C., tube to be directly diluted to 4 nM)
    c. THIRD 5 uL=for QC (1 uL BioAnalyzer and 2 uL DeNovix, −20° C.)
        i. IMPORTANT: Ensure there are no beads in this 3rd aliquot as they may interfere with BioAnalyzer results Example 4

Blood samples will be drawn from patients with suspected early knee osteoarthritis. K2-EDTA tubes containing blood will be centrifuged at 4000 rpm for 10 minutes at 4° C. to separate supernatant. The resulting plasma supernatant will be aliquotted into 250 uL per cryovial and subjected to isolation of RNA and microRNAs. Library preparation and sequencing analysis will be performed to determine the expression of the 11 microRNAs of interest.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

1. Ratneswaran A, Rockel J S, and Kapoor M. Understanding osteoarthritis pathogenesis: a multiomics system-based approach. *Curr Opin Rheumatol.* 2020; 32(1):80-91.
2. Pritchard C C, Cheng H H, and Tewari M. MicroRNA profiling: approaches and considerations. *Nat Rev Genet.* 2012; 13(5):358-69.
3. Nugent M. MicroRNAs: exploring new horizons in osteoarthritis. *Osteoarthritis Cartilage.* 2016; 24(4):573-80.
4. Wang Z, Lu Y, and Han J. Peripheral blood microRNAs: A novel tool for diagnosing disease? *Intractable Rare Dis Res.* 2012; 1(3):98-102.
5. Mitchell P S, Parkin R K, Kroh E M, Fritz B R, Wyman S K, Pogosova-Agadjanyan E L, et al. Circulating microRNAs as stable blood-based markers for cancer detection. *Proc Natl Acad Sci USA.* 2008; 105(30):10513-8.
6. Endisha H, Rockel J, Jurisica I, and Kapoor M. The complex landscape of microRNAs in articular cartilage: biology, pathology, and therapeutic targets. *JCI Insight.* 2018; 3 (17).
7. Coutinho de Almeida R, Ramos Y F M, Mahfouz A, den Hollander W, Lakenberg N, Houtman E, et al. RNA sequencing data integration reveals an miRNA interactome of osteoarthritis cartilage. *Ann Rheum Dis.* 2019; 78(2):270-7.
8. Bratus-Neuenschwander A, Castro-Giner F, Frank-Bertoncelj M, Aluri S, Fucentese S F, Schlapbach R, et al. Pain-Associated Transcriptome Changes in Synovium of Knee Osteoarthritis Patients. *Genes (Basel).* 2018; 9 (7).
9. Nakamura A, Rampersaud Y R, Sharma A, Lewis S J, Wu B, Datta P, et al. Identification of microRNA-181a-5p and microRNA-4454 as mediators of facet cartilage degeneration. *JCI Insight.* 2016; 1 (12): e86820.
10. Li Y H, Tavallaee G, Tokar T, Nakamura A, Sundararajan K, Weston A, et al. Identification of synovial fluid microRNA signature in knee osteoarthritis: differentiating early- and late-stage knee osteoarthritis. *Osteoarthritis Cartilage.* 2016; 24(9):1577-86.
11. Murata K, Yoshitomi H, Tanida S, Ishikawa M, Nishitani K, Ito H, et al. Plasma and synovial fluid microRNAs as potential biomarkers of rheumatoid arthritis and osteoarthritis. *Arthritis Res Ther.* 2010; 12 (3): R86.
12. Borgonio Cuadra V M, Gonzalez-Huerta N C, Romero-Cordoba S, Hidalgo-Miranda A, and Miranda-Duarte A. Altered expression of circulating microRNA in plasma of patients with primary osteoarthritis and in silico analysis of their pathways. *PLoS One.* 2014; 9 (6): e97690.
13. Beyer C, Zampetaki A, Lin N Y, Kleyer A, Perricone C, lagnocco A, et al. Signature of circulating microRNAs in osteoarthritis. *Ann Rheum Dis.* 2015; 74 (3): e18.
14. Ntoumou E, Tzetis M, Braoudaki M, Lambrou G, Poulou M, Malizos K, et al. Serum microRNA array analysis identifies miR-140-3p, miR-33b-3p and miR-671-3p as potential osteoarthritis biomarkers involved in metabolic processes. *Clin Epigenetics.* 2017; 9:127.
15. Aae T F, Karlsen T A, Haugen I K, Risberg M A, Lian Ø B, and Brinchmann J E. Evaluating plasma extracellular vesicle microRNAs as possible biomarkers for osteoarthritis. *Osteoarthritis and Cartilage Open.* 2020; 1(3):100018.
16. Rousseau J C, Millet M, Croset M, Sornay-Rendu E, Borel O, and Chapurlat R. Association of circulating microRNAs with prevalent and incident knee osteoarthritis in women: the OFELY study. *Arthritis Res Ther.* 2020; 22(1):2.

17. Altman R, Asch E, Bloch D, Bole G, Borenstein D, Brandt K, et al. Development of criteria for the classification and reporting of osteoarthritis. Classification of osteoarthritis of the knee. Diagnostic and Therapeutic Criteria Committee of the American Rheumatism Association. *Arthritis Rheum.* 1986; 29(8):1039-49.
18. Kellgren J H, and Lawrence J S. Radiological assessment of osteo-arthrosis. *Ann Rheum Dis.* 1957; 16(4):494-502.
19. Kok M G M, de Ronde M W J, Moerland P D, Ruijter J M, Creemers E E, and Pinto-Sietsma S J. Small sample sizes in high-throughput miRNA screens: A common pitfall for the identification of miRNA biomarkers. *Biomol Detect Quantif.* 2018; 15:1-5.
20. Ameling S, Kacprowski T, Chilukoti R K, Malsch C, Liebscher V, Suhre K, et al. Associations of circulating plasma microRNAs with age, body mass index and sex in a population-based study. *BMC Med Genomics.* 2015; 8:61.
21. Londin E, Loher P, Telonis A G, Quann K, Clark P, Jing Y, et al. Analysis of 13 cell types reveals evidence for the expression of numerous novel primate- and tissue-specific microRNAs. *Proc Natl Acad Sci USA.* 2015; 112 (10): E1106-15.
22. Tokar T, Pastrello C, Rossos A E M, Abovsky M, Hauschild A C, Tsay M, et al. mirDIP 4.1-integrative database of human microRNA target predictions. *Nucleic Acids Res.* 2018; 46 (D1): D360-D70.
23. Veksler-Lublinsky I, Shemer-Avni Y, Kedem K, and Ziv-Ukelson M. Gene bi-targeting by viral and human miRNAs. *BMC Bioinformatics.* 2010; 11:249.
24. Betel D, Koppal A, Agius P, Sander C, and Leslie C. Comprehensive modeling of microRNA targets predicts functional non-conserved and non-canonical sites. *Genome Biol.* 2010; 11 (8): R90.
25. Vejnar C E, and Zdobnov E M. MIRmap: comprehensive prediction of microRNA target repression strength. *Nucleic Acids Res.* 2012; 40(22):11673-83.
26. Pla A, Zhong X, and Rayner S. miRAW: A deep learning-based approach to predict microRNA targets by analyzing whole microRNA transcripts. *PLoS Comput Biol.* 2018; 14 (7): e1006185.
27. Rahmati S, Abovsky M, Pastrello C, Kotlyar M, Lu R, Cumbaa C A, et al. pathDIP 4: an extended pathway annotations and enrichment analysis resource for human, model organisms and domesticated species. *Nucleic Acids Res.* 2019.
28. Brown K R, Otasek D, Ali M, McGuffin M J, Xie W, Devani B, et al. NAViGaTOR: Network Analysis, Visualization and Graphing Toronto. *Bioinformatics.* 2009; 25(24):3327-9.
29. Ramos Y F, Bos S D, Lakenberg N, Bohringer S, den Hollander W J, Kloppenburg M, et al. Genes expressed in blood link osteoarthritis with apoptotic pathways. *Ann Rheum Dis.* 2014; 73(10):1844-53.
30. Wang Q, Rozelle A L, Lepus C M, Scanzello C R, Song J J, Larsen D M, et al. Identification of a central role for complement in osteoarthritis. *Nat Med.* 2011; 17(12):1674-9.
31. Luyten F P, Bierma-Zeinstra S, Dell'Accio F, Kraus V B, Nakata K, Sekiya I, et al. Toward classification criteria for early osteoarthritis of the knee. *Semin Arthritis Rheum.* 2018; 47(4):457-63.
32. Hunter D J, Nevitt M, Losina E, and Kraus V. Biomarkers for osteoarthritis: current position and steps towards further validation. *Best Pract Res Clin Rheumatol.* 2014; 28(1):61-71.
33. Kraus V B, Collins J E, Hargrove D, Losina E, Nevitt M, Katz J N, et al. Predictive validity of biochemical biomarkers in knee osteoarthritis: data from the FNIH OA Biomarkers Consortium. *Ann Rheum Dis.* 2017; 76(1): 186-95.
34. Robinson M D, and Oshlack A. A scaling normalization method for differential expression analysis of RNA-seq data. *Genome Biol.* 2010; 11 (3): R25.
35. Shen J, Li S, and Chen D. TGF-beta signaling and the development of osteoarthritis. *Bone Res.* 2014; 2.
36. Chen Y J, Chang W A, Huang M S, Chen C H, Wang K Y, Hsu Y L, et al. Identification of novel genes in aging osteoblasts using next-generation sequencing and bioinformatics. *Oncotarget.* 2017; 8(69):113598-613.
37. Tornero-Esteban P, Rodriguez-Rodriguez L, Abasolo L, Tome M, Lopez-Romero P, Herranz E, et al. Signature of microRNA expression during osteogenic differentiation of bone marrow MSCs reveals a putative role of miR-335-5p in osteoarthritis. *BMC Musculoskelet Disord.* 2015; 16:182.
38. Lin X, Wu L, Zhang Z, Yang R, Guan Q, Hou X, et al. MiR-335-5p promotes chondrogenesis in mouse mesenchymal stem cells and is regulated through two positive feedback loops. *J Bone Miner Res.* 2014; 29(7):1575-85.
39. Nakamura A, Rampersaud Y R, Nakamura S, Sharma A, Zeng F, Rossomacha E, et al. microRNA-181a-5p antisense oligonucleotides attenuate osteoarthritis in facet and knee joints. *Ann Rheum Dis.* 2019; 78(1):111-21.
40. Anders S, and Huber W. Differential expression analysis for sequence count data. *Genome Biol.* 2010; 11 (10): R106.
41. Lund S P, Nettleton D, McCarthy D J, and Smyth G K. Detecting differential expression in RNA-sequence data using quasi-likelihood with shrunken dispersion estimates. *Stat Appl Genet Mol Biol.* 2012; 11 (5).
42. Friedlander M R, Mackowiak S D, Li N, Chen W, and Rajewsky N. miRDeep2 accurately identifies known and hundreds of novel microRNA genes in seven animal clades. *Nucleic Acids Res.* 2012; 40(1):37-52.
43. Dassi E, Re A, Leo S, Tebaldi T, Pasini L, Peroni D, et al. AURA 2: Empowering discovery of post-transcriptional networks. *Translation (Austin).* 2014; 2 (1): e27738.
44. Di Tommaso P, Chatzou M, Floden E W, Barja P P, Palumbo E, and Notredame C. Nextflow enables reproducible computational workflows. *Nat Biotechnol.* 2017; 35(4):316-9.
45. Yoo A B, Jette M A, and Grondona M. Berlin, Heidelberg: Springer Berlin Heidelberg; 2003:44-60.
46. Huang H, Zheng J, Shen N, Wang G, Zhou G, Fang Y, et al. Identification of pathways and genes associated with synovitis in osteoarthritis using bioinformatics analyses. *Sci Rep.* 2018; 8(1):10050.
47. Kotlyar M, Pastrello C, Malik Z, and Jurisica I. IID 2018 update: context-specific physical protein-protein interactions in human, model organisms and domesticated species. *Nucleic Acids Res.* 2019; 47 (D1): D581-D9.
48. Anders, S. and W. Huber, Differential expression analysis for sequence count data. *Genome Biol,* 2010. 11 (10): p. R106.
49. Krepelkova I, Mrackova T, Izakova J, Dvorakova B, Chalupova L, Mikulik R, Slaby O, Bartos M, Ruzicka V. Evaluation of miRNA detection methods for the analytical characteristic necessary for clinical utilization. Biotechniques. 2019 June; 66(6):277-284.

We claim:

1. A method comprising:
   a) obtaining a substantially cell-free sample of blood plasma or blood serum from a subject with knee osteoarthritis; and
   b) detecting the presence of, and optionally measuring the level of, SEQ ID NOs: 1-4 in the sample.

2. The method of claim 1, wherein the method further comprises detecting the presence of, and optionally measuring the level of, SEQ ID NO: 5 in the sample.

3. The method of claim 1, wherein the method further comprises detecting the presence of, and optionally measuring the level of, SEQ ID NO: 6 in the sample.

4. The method of claim 1, wherein the method comprises detecting the presence of, and optionally measuring the level of, at least 4, at least 5, at least 6, at least 7, at least 8, at least 9, at least 10, or at least 11 miRNAs.

5. The method of claim 1, wherein (b) comprises use of one or more probes, optionally nucleic acid probes, optionally cDNA probes or stabilized RNA probes that hybridize to a target miRNA.

6. The method of claim 1, wherein (b) comprises use of RT-PCR, optionally quantitative RT-PCR and/or sequencing, optionally wherein the sequencing comprises use of unique molecular indexes (UMIs) during cDNA synthesis.

7. The method of claim 1, wherein the method further comprises detecting the presence of, and optionally measuring the level of, SEQ ID NO: 7 in the sample.

8. The method of claim 1, wherein the method further comprises detecting the presence of, and optionally measuring the level of, SEQ ID NO: 8 in the sample.

9. The method of claim 1, wherein the method further comprises detecting the presence of, and optionally measuring the level of, SEQ ID NO: 9 in the sample.

10. The method of claim 5, wherein the one or more probes comprise at least 80% or at least 90% sequence identity to the complement of a miRNA.

11. The method of claim 1, wherein the method further comprises detecting the presence of, and optionally measuring the level of, SEQ ID NO: 10 in the sample.

12. The method of claim 1, wherein the method further comprises detecting the presence of, and optionally measuring the level of, SEQ ID NO: 11 in the sample.

13. The method of claim 1, wherein the method further comprises detecting the presence of, and optionally measuring the level of, SEQ ID NO: 12 in the sample.

14. The method of claim 1, wherein the method further comprises detecting the presence of, and optionally measuring the level of, SEQ ID NO: 13 in the sample.

15. The method of claim 1, wherein the method further comprises detecting the presence of, and optionally measuring the level of, hsa-miR-335-3p in the sample.

16. The method of claim 1, wherein the method further comprises detecting the presence of, and optionally measuring the level of, hsa-miR-199a-5p in the sample.

17. The method of claim 1, wherein the method further comprises detecting the presence of, and optionally measuring the level of, hsa-miR-671-3p in the sample.

18. The method of claim 1, wherein the method further comprises detecting the presence of, and optionally measuring the level of, hsa-miR-1260b in the sample.

19. The method of claim 1, wherein the method further comprises detecting the presence of, and optionally measuring the level of, hsa-miR-191-3p in the sample.

20. The method of claim 1, wherein the method further comprises detecting the presence of, and optionally measuring the level of, hsa-miR-335-5p in the sample.

21. The method of claim 1, wherein the method further comprises detecting the presence of, and optionally measuring the level of, hsa-miR-543 in the sample.

22. The method of claim 1, wherein the method further comprises detecting the presence of, and optionally measuring the level of, hsa-miR-335-3p, hsa-miR-199a-5p, hsa-miR-671-3p, hsa-miR-1260b, hsa-miR-191-3p, hsa-miR-335-5p, and hsa-miR-543 in the sample.

* * * * *

SEQUENCE LISTING

<160> NUMBER OF SEQ ID NOS: 13

<210> SEQ ID NO 1
<211> LENGTH: 18
<212> TYPE: RNA
<213> ORGANISM: Homo Sapiens

<400> SEQUENCE: 1
gucuggcuca ggguugggg                                                     18

<210> SEQ ID NO 2
<211> LENGTH: 19
<212> TYPE: RNA
<213> ORGANISM: Homo Sapiens

<400> SEQUENCE: 2
ucccuguucg ggcgccacu                                                     19

<210> SEQ ID NO 3
<211> LENGTH: 22
<212> TYPE: RNA
<213> ORGANISM: Homo Sapiens

<400> SEQUENCE: 3
uguuuagcau ccuguagccu gc                                                 22

<210> SEQ ID NO 4
<211> LENGTH: 18
<212> TYPE: RNA
<213> ORGANISM: Homo Sapiens

<400> SEQUENCE: 4
uaguggguua ucagaacu                                                      18

<210> SEQ ID NO 5
<211> LENGTH: 22
<212> TYPE: RNA
<213> ORGANISM: Homo Sapiens

<400> SEQUENCE: 5 acugaggga ugaaggauca gg                                                  22

<210> SEQ ID NO 6
<211> LENGTH: 18
<212> TYPE: RNA
<213> ORGANISM: Homo Sapiens

<400> SEQUENCE: 6
caugaaugga uuaaugag                                                      18

<210> SEQ ID NO 7
<211> LENGTH: 21
<212> TYPE: RNA
<213> ORGANISM: Homo Sapiens

<400> SEQUENCE: 7
ugguccaacg acaggaguag g                                                  21

<210> SEQ ID NO 8
<211> LENGTH: 22
<212> TYPE: RNA
<213> ORGANISM: Homo Sapiens

<400> SEQUENCE: 8

```
gaugccuggg aguugcgauc ug                                              22

<210> SEQ ID NO 9
<211> LENGTH: 22
<212> TYPE: RNA
<213> ORGANISM: Homo Sapiens

<400> SEQUENCE: 9
uuaguggcuc ccucugccug ca                                              22

<210> SEQ ID NO 10
<211> LENGTH: 18
<212> TYPE: RNA
<213> ORGANISM: Homo Sapiens

<400> SEQUENCE: 10
aggaaggugg ggaugacg                                                   18

<210> SEQ ID NO 11
<211> LENGTH: 21
<212> TYPE: RNA
<213> ORGANISM: Homo Sapiens

<400> SEQUENCE: 11
uugaggucgg acaugguggc u                                               21

<210> SEQ ID NO 12
<211> LENGTH: 17
<212> TYPE: RNA
<213> ORGANISM: Homo Sapiens

<400> SEQUENCE: 12
acuagggaug ggggaau                                                    17

<210> SEQ ID NO 13
<211> LENGTH: 18
<212> TYPE: RNA
<213> ORGANISM: Homo Sapiens

<400> SEQUENCE: 13
aggaguggga ggagaaug                                                   18
```